United States Patent [19]

Kadow et al.

[11] Patent Number: 4,958,010

[45] Date of Patent: Sep. 18, 1990

[54] EPIPODOPHYLLOTOXIN GLUCOSIDE LACTAM DERIVATIVES

[75] Inventors: John F. Kadow, Meriden; Dolatrai M. Vyas, Madison, both of Conn.

[73] Assignee: Bristol-Myers Company, New York, N.Y.

[21] Appl. No.: 302,010

[22] Filed: Jan. 30, 1989

Related U.S. Application Data

[63] Continuation-in-part of Ser. No. 156,253, Feb. 16, 1988, abandoned.

[51] Int. Cl.[5] .................. C07H 15/20; C07H 17/00
[52] U.S. Cl. ..................... 536/17.2; 536/17.1; 536/17.3; 536/17.4; 536/17.6; 536/18.1; 536/18.2; 514/33; 514/35
[58] Field of Search ............ 536/17.4, 18.1, 18.2, 536/17.2, 17.3, 17.6, 17.1; 514/27, 33, 35

[56] References Cited

U.S. PATENT DOCUMENTS

| | | | |
|---|---|---|---|
| 2,977,359 | 3/1961 | Rutschmann . | |
| 3,408,441 | 10/1968 | von Wartburg et al. | 536/18.1 |
| 3,524,844 | 8/1970 | Keller-Juslan et al. | 536/18.1 |
| 4,564,675 | 1/1986 | Kurabayashi et al. | 536/18.1 |

OTHER PUBLICATIONS

Rutschmann et al.; Helv. Chim. Acta 42:890–907 (1959).
Vaitkevicius et al.; Cancer Chemoth. Rep. 50:565–571 (1966).
Jardine et al.; J. Med. Chem. 25 (9):1077–1081 (1982).
Dow et al.; Cancer Res. 43(12, Pt. 1): 5699–5706 (1983).
Sinkule et al.; J. Pharm. Sci. 73(2): 164–168 (1984).
Anjanamurthy et al.; Indian J. Chem. 26B:131–135 (1987).

*Primary Examiner*—Ronald W. Griffin
*Assistant Examiner*—Nancy S. Carson
*Attorney, Agent, or Firm*—Mollie M. Yang

[57] ABSTRACT

Novel antitumor epipodophyllotoxin glucoside lactam derivatives are prepared by first converting the lactone ring of the parent compound to the open-chain trans-hydroxy hydrazide, condensing the hydrazide with a carbonyl compound to form the corresponding hydrazone, and finally cyclizing the trans-hydroxy hydrazone using diethylazodicarboxylate and triphenylphosphine.

41 Claims, No Drawings

EPIPODOPHYLLOTOXIN GLUCOSIDE LACTAM DERIVATIVES

This application is a continuation-in-part of U.S. patent application, Ser. No. 156,253, filed Feb. 16, 1988, now abandoned.

BACKGROUND OF THE INVENTION

1. Field of the Invention

The present invention relates to epipodophyllotoxin glucoside derivatives, to their use as tumor-inhibiting substances, to pharmaceutical compositions containing the novel compounds, and to intermediates for their preparation. More particularly, the novel antitumor compounds are lactam analogs of epipodophyllotoxin glucosides.

2. Background Art

Etoposide (Ia) and teniposide (Ib) are clinically useful anticancer agents derived from the naturally occurring lignan, podophyllotoxin. Currently etoposide is marketed in the United States under the trade name Vepesid for the treatment of small cell lung cancer and testicular cancer.

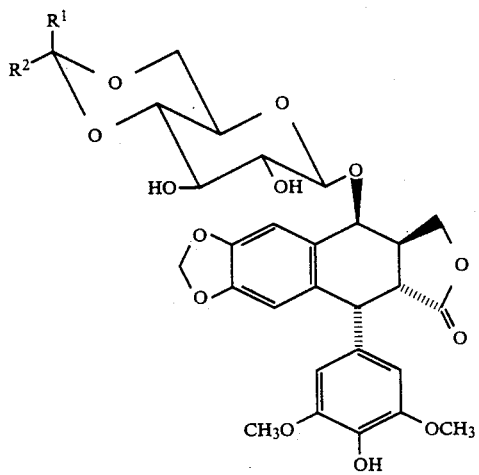

Ia: $R^1 = H$; $R^2 = CH_3$
Ib: $R^1 = H$; $R^2 = $ 2-thienyl

Podophyllotoxin and its derivatives have a highly strained trans-fused lactone ring in which the α-carbon is particularly prone to base-induced epimerization to give the thermodynamically more stable cis-fused lactone (picro form). The picro compounds have greatly diminished biological activities compared to the parent compounds. In vivo, etoposide is extensively metabolized to the open ring hydroxy acid. Thus an object of the present invention is to provide antitumor derivatives of epipodophyllotoxin glucoside which are more resistant to epimerization and/or less susceptible to deactivation by ring opening in vivo.

Epipodophyllotoxin glucosides and the methods for their preparation are disclosed in U.S. Pat. No. 3,408,441 awarded to Wartburg et al and U.S. Pat. No. 3,524,844 to Keller-Juslen et al. These compounds, in particular etoposide, serve as starting materials for our synthesis of compounds of the present invention.

U.S. Pat. No. 2,977,359 discloses the ring opening of podophyllotoxin with hydrazine to provide selectively either the cis-hydrazide (IIa) or the trans-hydrazide (IIb), the stereospecific reduction of the hydrazides to the corresponding hydroxy amides (IIIa and IIIb) using Raney nickel in ethanol, and the reaction of the hydrazides with aldehydes or ketones to provide the corresponding hydrazones (IVa and IVb). Although the amides and hydrazones are said to have anti-mitotic activity, no data showing such property are given in the patent specification.

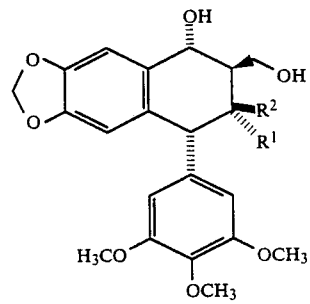

IIa: $R^1 = H$; $R^2 = -C(O)NHNH_2$
IIb: $R^1 = -C(O)NHNH_2$; $R^2 = H$
IIIa: $R^1 = H$; $R^2 = -C(O)NH_2$
IIIb: $R^1 = -C(O)NH_2$; $R^2 = H$
IVa: $R^1 = H$; $R^2 = C(O)NHN=CR^3R^4$
IVb: $R^1 = -C(O)NHN=CR^3R^4$; $R^2 = H$

The use of substituted hydrazines in this ring opening reaction has also been reported (Helv. Chim. Acta, 1959, 42:890-907). The ethyl hydrazide of podophyllotoxin (V) underwent clinical trials but showed minimal antitumor activity (Cancer Chemoth. Rep., 1966, 50:565-571).

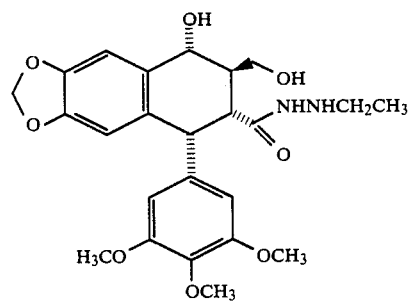

Also reported in the Helv. Chim. Acta paper, supra. are the hydrazides of 4'-demethylpodophyllotoxin and epipodophyllotoxin.

The preparation of the lactam of β-apopicropodophyllin (VI) from β-apopicropodophyllin and ammonia is described in Indian J. Chem., 1987, 26B: 131–5.

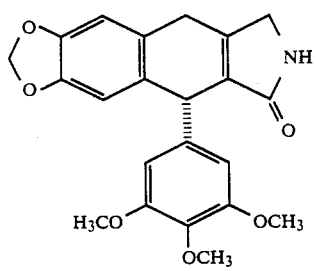

SUMMARY OF INVENTION

The present invention provides antitumor compounds having formulas (VII) and (VIII)

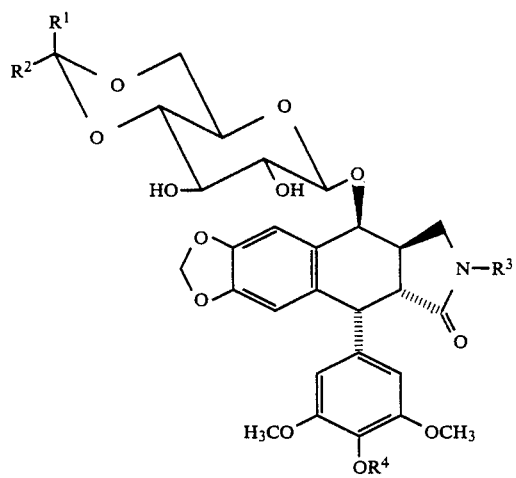

VII

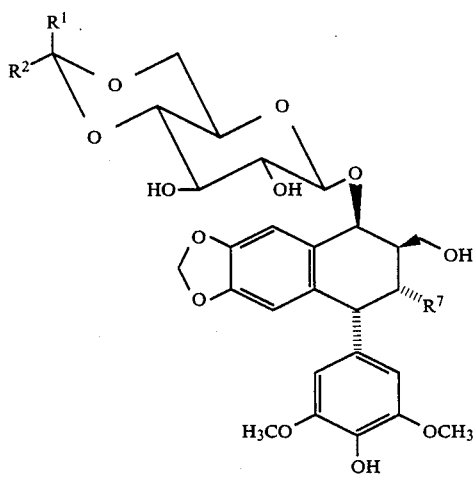

VIII wherein $R^1$ and $R^2$ are each $C_{1-10}$alkyl; or $R^1$, $R^2$, and the carbon to which they are attached represent $C_{5-6}$cycloalkyl; or $R^1$ is H and $R^2$ is selected from the group consisting of $C_{1-10}$aklyl, $C_{2-10}$alkenyl, $C_{3-6}$cycloalkyl, furyl, thienyl, $C_{6-10}$aryl, and $C_{7-14}$aralkyl; $R^3$ is selected from the group consisting of H, —$NH_2$, —$N=CR^5R^6$, and wherein $R^5$ and $R^6$ are the same or different groups selected from H, $C_{1-10}$alkyl, $C_{2-10}$alkenyl, $C_{3-6}$cycloalkyl, $C_{6-10}$aryl, $C_{7-14}$aralkyl, and heteroaryl; each of the above is optionally substituted with one or more same or different groups selected from the group consisting of $C_{1-5}$alkoxy, hydroxy, amino, $C_{1-5}$alkylamino, di($C_{1-5}$alkyl)amino, nitro, halogen, $C_{1-5}$haloalkyl, $C_{1-5}$dihaloalkyl, $C_{1-5}$trihaloalkyl, cyano, $C_{1-5}$alkylthio, mercapto, alkanoyl, carbamoyl, carboxy, and alkanoylamino; the substituent for aryl, aralkyl and heteroaryl includes additionally $C_{1-5}$alkyl; $R^4$ is selected from the group consisting of H, alkanoyl, aroyl, aralkanoyl and P(O)(OM)(OM') wherein M and M' are independently selected from the group consisting of H, an alkali metal cation and phenyl; and $R^7$ is —C(O)$NH_2$ or —C≡N.

A preferred embodiment provides compounds of formulas (VII) and (VIII) wherein $R^1$ is H and $R^2$ is methyl or 2-thienyl.

A further preferred embodiment provides compounds of formula (VII) wherein $R^3$ is selected from the group consisting of H, —$NH_2$, —$N=CR^5R^6$, and —$NHCHR^5R^6$; wherein $R^5$ and $R^6$ are the same or different $C_{1-10}$alkyl; or $R^5$ is H and $R^6$ is $C_{1-10}$alkyl or phenyl optionally substituted on the ring with nitro; $R^4$ is H or P(O)(OM)(OM') wherein M and M' are as above-defined. More preferably, $R^5$ and $R^6$ are the same or different $C_{1-3}$ alkyl; or $R^5$ is H and $R^6$ is $C_{1-10}$alkyl or phenyl; and $R^4$ is H or P(O)(OH)$_2$ or an alkali metal salt thereof. Compounds wherein $R^4$ is P(O)(OH)$_2$ or an alkali metal salt thereof are water soluble prodrugs.

A further aspect of the present invention provides intermediates of the formula (IX)

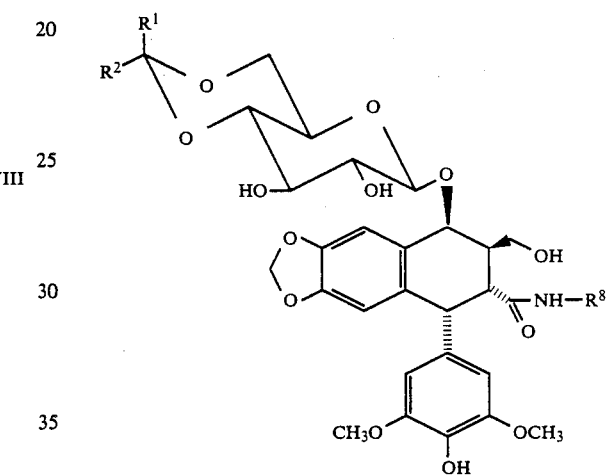

wherein $R^8$ is —$NH_2$ or —$N=CR^5R^6$; and $R^1$, $R^2$, $R^5$ and $R^6$ are as defined above for formula (VII).

A further aspect of the present invention provides a method for inhibiting mammalian tumor growth which comprises administering to a tumor-bearing host tumor inhibiting amount of a compound of formula (VII) or (VIII).

Yet another aspect of the present invention provides a pharmaceutical composition which comprises a tumor-inhibiting amount of a compound of formulas (VII) or (VIII) and a pharmaceutically acceptable carrier.

DETAILED DESCRIPTION OF THE INVENTION

As used here in the term "alkyl" encompasses straight and branched carbon chains; "alkenyl" means straight and branched carbon chains having at least one carbon-carbon double bond; "halo" or "halogen" includes fluorine, chlorine, bromine, and iodine; and "heteroaryl" means an aromatic ring containing at least one non-carbon atom, for example, pyridine, thiophene, furan, imidazole, pyrrole, thiazole, and isoxazole. Systematic names are provided for compounds specifically exemplified. This nomenclature, however, is complicated and cumbersome; thus, for ease of discussion, a series of trivial designations illustrated with structural diagrams are used throughout the specification.

Antitumor compounds of the present invention may be prepared from the corresponding 4'-demethylepipodophyllotoxin glucosides via the trans-hydroxy hydrazides (X). In general, strongly acidic and basic reaction conditions are best avoided as the glycosidic linkage is acid sensitive and the α-carbon of the lactone is prone to base-promoted epimerization.

A 4'-demethylepipodophyllotoxin glucoside (I, wherein $R^1$ and $R^2$ are as defined in formula VII) is heated with hydrazine to yield a mixture of trans- and cis- hydroxy hydrazides. The reaction is carried out in an organic solvent such as a lower aliphatic alcohol, e.g. methanol, and advantageously in the presence of a mild acid to preferably at the refluxing temperature of the reaction mixture. The Raney nickel may be washed with water or an alcohol prior to its use to ensure its neutrality. Although Ra-Ni is the preferred agent for reductively cleaving the N-N bond, other reagents that can effect such cleavage may also be used, for example nickel-/aluminum alloy. The hydroxy amide may be further transformed into the nitrile (XII) by using a dehydrating agent, e.g. tosyl chloride, phosphorus pentoxide, $POCl_3$, $PCl_5$, and thionyl chloride; tosyl chloride in the presence of a hydrogen chloride binding agent, e.g.

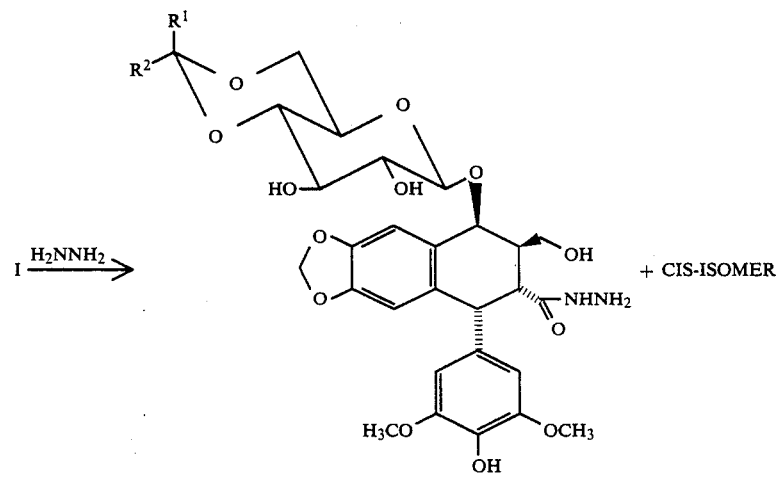

minimize the formation of the cis- isomer; a carboxylic acid such as acetic acid may be suitably so employed. Surprisingly, the cis- isomer derived from etoposide readily precipitates from the reaction solution thus enabling the easy separation of the desired trans- isomer. In general the cis- and trans- isomers are separable chromatographically.

The trans-hydroxy hydrazide is converted to the corresponding hydroxy amide (XI) by treatment with Raney nickel (Ra-Ni) in a lower aliphatic alcohol such as ethanol. The reaction is carried out at elevated temperature, pyridine or another tertiary amine base, is the preferred reagent.

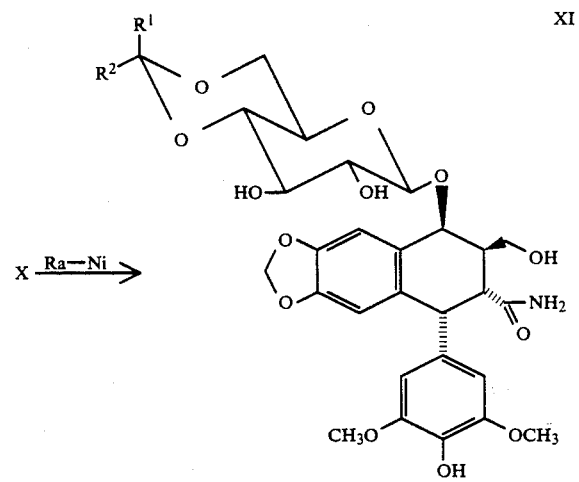

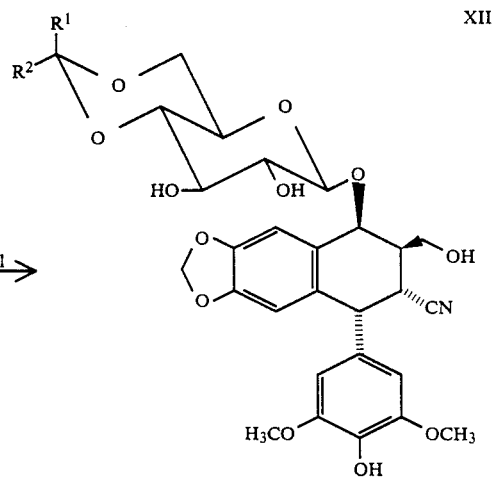

The trans-hydroxy hydrazide is readily converted into the corresponding hydrazone (XIII) by reaction with an aldehyde or a ketone; the carbonyl compound is preferably

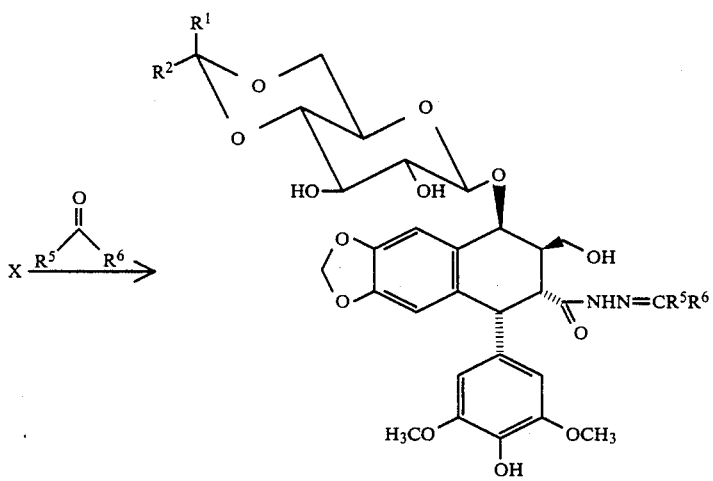

used in excess relative to the hydrazide. The reaction may be carried out in an inert organic solvent or a mixture of solvents such as methylene chloride and methanol; or where appropriate the carbonyl compound itself may serve as the solvent. The temperature and length of reaction depend on the reactivity of the specific carbonyl compound used.

The hydroxy hydrazones (XIII) are cyclized to the lactam hydrazone (XIV) with dialkylazodicarboxylate and a tertiary phosphine in an aprotic organic solvent such as tetrahydrofuran or acetonitrile at ambient temperature. The combination of diethylazodiacarboxylate (DEAD) and triphenylphosphine is preferred. In some cases the cyclization

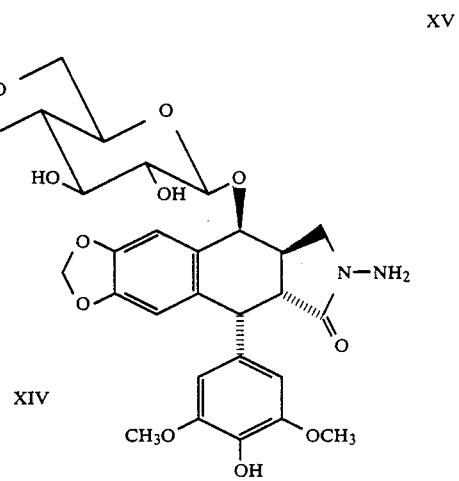

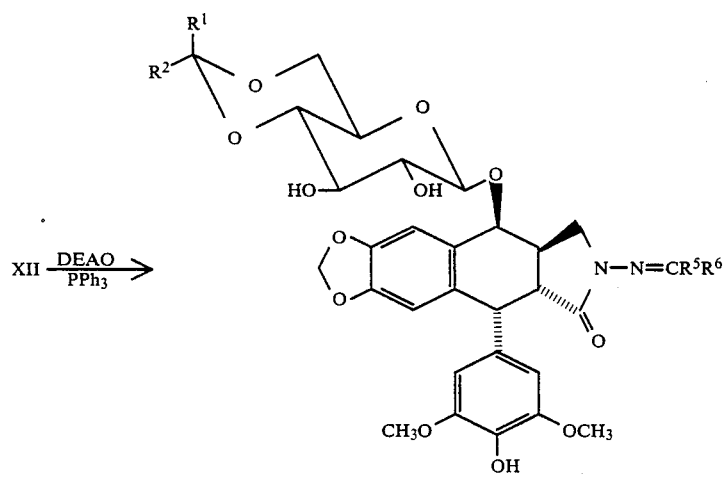

may result in an inseparable mixture of O- cyclized and N- cyclized products (cyclic imino ether and lactam compounds, respectively). The mixture may be directly subjected to alcoholysis whereby the N-cyclized product is preferentially cleaved to yield the lactam hydrazide (XV) and the carbonyl compound. The lactam hydrazide may be separated from the reaction mixture using conventional separation methodologies such as column chromatography. Of course, lactam hydrazides may be obtained as hydrolysis products of lactam hydrazones (XIV) that had been isolated. Lactam hydrazides can also serve as intermediates to prepare lactam hydrazones that might otherwise be difficult to make via the aforementioned cyclization method.

Lactam hydrazone (XIV) may be hydrogenated to produce the N-substituted lactam hydrazide (XVI). The hydrogenation is performed in the presence of a suitable catalyst which does not affect the C=O or N—N bonds; catalysts that may be used include palladium and other noble metal catalysts. Lactam hydrazone (XIV) may be subjected to reductive cleavage of the N—N bond using Raney nickel or nickel/aluminum alloy under conditions described above to give the lactam (XVII).

diphenylchlorophosphate, ClP(O)(OPh)2, in the presence of a base, for example diisopropylethylamine, and in an inert organic solvent such as acetonitrile. The lactam hydrazone diphenylphosphate (VII, $R^3$=N=$CR^5R^6$ and $R^4$=P(O)(OPh)$_2$) thus obtained may be converted to the lactam diphenylphosphate (VII, $R^3$=H and $R^4$=P(O)(OPh)$_2$) by treatment with Raney nickel in refluxing ethanol according to the procedure outlined above. Hydrogenolysis of the lactam diphenylphosphate in the presence of a catalyst such as

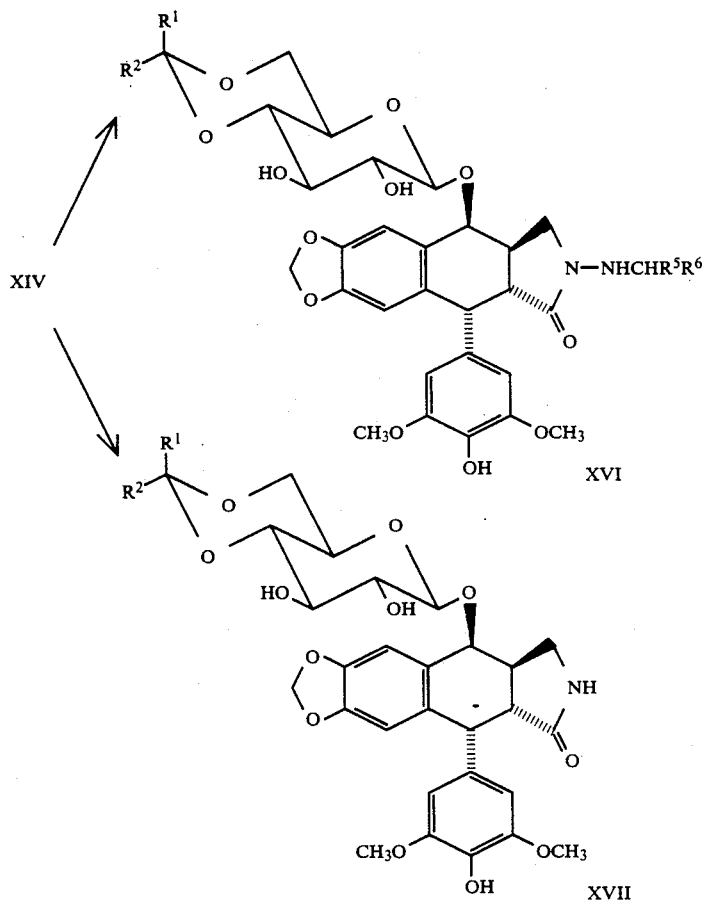

Compounds of formula (VII) wherein —$OR^4$ represents an ester moiety are produced when the corresponding phenol group is reacted with an acylating agent generally known in the art, examples of which include carboxylic acid in the presence of a condensing agent such as dicyclohexylcarbodiimide; symmetrical or mixed acid anhydride; active ester; active amide; and acid halide. Acid halide is the preferred acylating agent and the reaction is conducted in a suitable anhydrous organic solvent such as acetonitrile, tetrahydrofuran, and acetone, and in the presence of a suitable base to neutralize the hydrogen chloride formed during the course of the reaction. Suitable bases are for example tertiary amine such as diisopropylethylamine and inorganic bases such as potassium carbonate and sodium carbonate. In our experience, we have found acetonitrile to be the preferred solvent with diisopropylethylamine being the preferred base.

Diphenylphosphate of lactam hydrazones (VII, $R^3$=N=$CR^5R^6$ wherein $R^5$ and $R^6$ are as previously defined, and $R^4$ is P(O)(OPh)$_2$) may be prepared by reacting the corresponding 4'-phenol compound with platinum oxide provides the corresponding dihydrogen phosphate (VII, R=H and $R^4$=P(O)(OH)$_2$) which is converted into the base salt upon treatment with an alkali metal base, for example sodium or potassium carbonate or bicarbonate. The lactam hydrazone diphenylphosphate may also be hydrolyzed in a water miscible solvent such as dioxane, and in the presence of an acid to give the lactam hydrazide diphenylphosphate (VII, $R^3$=NH$_2$ and $R^4$=P(O)(OPh)$_2$). Or, by judicious selection of reaction conditions and catalyst the N=C double bond of the lactam hydrazone diphenylphosphate may be selectively reduced by hydrogenation to provide the diphenylphosphate of substituted lactam hydrazide (VII, $R^3$=NHCHR$^5$R$^6$, $R^4$=P(O)(OPh)$_2$); a suitable catalyst for this reaction may be for example palladium on carbon.

The dihydrogen phosphate of the lactam hydrazone (VII, $R^3$ and $R^4$=P(O)(OH) ) and alkali metal salts thereof may be prepared by reacting the 4'-phenol compound with phosphorous oxychloride in the presence of a tertiary amine base, followed by hydrolysis of the dichlorophosphate intermediate. When the hydrolysis is performed in the presence of an alkali metal base such as sodium bicarbonate, the alkali metal salt is obtained. The lactam hydrazone dihydrogen phosphate may be converted into lactam hydrazide dihydrogen phosphate or substituted lactam hydrazide dihydrogen phosphate by procedures discussed in the preceding paragraph.

BIOLOGICAL ACTIVITY

Representative compounds of the present invention have been evaluated in transplantable murine P388 leukemia. $CDF_1$ mice were implanted intraperitoneally with a tumor inoculum of $10^6$ ascites cells of P388 leukemia and treated with various doses of a test compound. A group of four mice was used for each dose level. Ten mice treated with saline were included in each series of experiments as negative control and six etoposide treated mice were included as positive control. The drugs were administered intraperitoneally on days 5 and 8 (day 1 being the day of tumor implantation). The length of the experiments ranges from 30 days to 47 days. At the end of the experiments the number of survivors for each group was noted. The mean survival time for each group of mice was determined and antitumor activity was expressed as % T/C which is the ratio of the median survival time (MST) of drug-treated group to the MST of saline-treated control group. A compound showing a % T/C value of 125 or greater is generally considered to have significant antitumor activity in the P388 test. Table I presents the results of the above-described evaluation; included in the Table are the maximum % T/C and the dose showing the maximum effect.

TABLE I

| Antitumor Activity in P388 Murine Leukemia | | |
|---|---|---|
| Compound of Example | Dose (mg/kg/dose) | Max % T/C |
| 2 | 180 | 135 |
| etoposide | 100 | 235 |
| 3 | 140 | 135 |
| 4 | 160 | 135 |
| 5 | 160 | 185 |
| etoposide | 80 | 295 |
| 6 | 70 | 123 |
| etoposide | 80 | 241 |
| 8 | 160 | 205 |
| 9 | 160 | 170 |
| 12 | 140 | 150 |
| etoposide | 60 | 250 |
| 10 | 40 | 100 |
| 11 | 160 | 140 |
| etoposide | 100 | >140 |
| 7 | 240 | 200 |
| etoposide | 100 | 260 |

Compound of Example 15 was evaluated against intravenously implanted P388 leukemia ($10^6$ cells) in $BDF_1$ female mice. The test compound was administered intravenously at various dose levels to groups of six mice on days 5 and 8; the positive control, etoposide, was given intraperitoneally. The experiment lasted 64 days. Compound of Example 15 showed a max. % T/C of 235 at a dose of 200 mg/kg/dose and etoposide showed a max. % T/C of >753 at 125 mg/kg/dose.

Representative compounds of the present invention were also evaluated in in vitro cytotoxicity assay against various murine and human tumor cell lines. The in vitro cytotoxicity assay involved growing various mammalian tumor cells, including human tumor cells, on microtitre plates employing established tissue culture methods. The concentration of each compound required to inhibit cell growth by 50% ($IC_{50}$) was then determined by four-fold serial dilution technique. Tumor cells of the following types were employed for each compound tested: B16-F10 murine melanoma; Moser human colon; SW900 human lung; and two human colon tumor cell lines namely HCT-116, and HCT/VP35, the latter being resistant to etoposide (VP). Table II shows the results of the in vitro assays. In general, $IC_{50}$ values of 250 and less are indicative of significant activity. The in vitro data may also be evaluated in terms of potency ratio which is defined as the ratio of $IC_{50}$ against an etoposide-resistant cell-line to $IC_{50}$ against an etoposide-sensitive cell-line. Compounds havig potency ratios lower than those of etoposide may then be interpreted as being more active than etoposide in resistant cell-line at an equivalent dose. For example, the potency ratios $IC_{50}$ HCT/VP35:IC HCT-116 for compounds of examples 10 and 11 are 1; whereas in the same experiment the ratios for etoposide range from 3 to 9.

TABLE II

| In vitro cytotoxicity against tumor cell lines | | | | | |
|---|---|---|---|---|---|
| Compound of | $IC_{50}$ (µg/ml) | | | | |
| Example # | B16-F10 | HCT-116 | HCT/VP35 | Moser | SW900 |
| 8 | 43.23 | 69.40 | 102.60 | 91.26 | >250 |
|  | 61.29 | 78.90 | 96.26 | 123.63 | >250 |
|  | 74.21 | 108.89 |  | >250 | >250 |
| 9 | 6.64 | 3.39 | 6.85 | 11.51 | 21.21 |
|  | 6.70 | 4.68 | 23.65 | 15.09 | 52.18 |
|  | 10.21 | 16.63 |  | 15.98 | 95.53 |
| Etoposide | 19.36 | 15.21 | 16.31 | 94.51 | 213.23 |
|  | 51.93 | 30.12 | 18.74 | 97.83 | 241.88 |
|  | 62.19 | 51.27 | 140.63 | 116.41 |  |
| 2 | 70.59 | 78.59 | >250 | 107.35 | 105.86 |
|  | 93.03 | 96.28 | >250 | 115.67 | 120.54 |
| 3 | 10.34 | 23.79 | 38.32 | 56.44 | 36.50 |
|  | 17.80 | 20.04 | 42.37 | 73.81 | 48.73 |
| 4 | 73.37 | 104.78 | >250 | 122.94 | >250 |
|  | 95.19 | 113.88 | >250 | >250 | >250 |
| 5 | 27.92 | 56.14 | 102.90 | 81.09 | 107.34 |
|  | 72.27 | 66.52 | 111.78 | 102.51 | 123.53 |
| 6 | 7.73 | 83.56 | >250 | >250 | >250 |
|  | 16.11 | 60.66 | >250 | >250 | >250 |
| etoposide | 9.96 | 3.86 | 79.06 | 65.72 | 77.80 |
|  | 5.80 | 6.57 | 48.22 | 54.09 | 54.59 |
| 10 | 16.76 | 16.05 | 13.50 | 16.38 | 19.82 |
|  | 23.65 | 17.26 | 25.58 | 25.60 | 21.22 |
| 11 | 20.99 | 17.26 | 18.67 | 20.23 | 12.33 |
|  | 20.69 | 18.33 | 25.22 | 25.92 | 12.48 |
| etoposide | 16.75 | 14.78 | 122.79 | 121.73 | 201.94 |
|  | 19.47 | 20.54 | 184.01 | 163.19 | 241.29 |
|  | 27.72 | 38.03 | 98.33 | 208.30 | 243.49 |
|  | 30.38 | 41.01 | 142.90 | 209.76 | >500 |

As indicated by the in vivo and in vitro test data provided above, compounds of present invention exhibit useful tumor cell growth inhibiting properties.

The invention includes within its scope pharmaceutical compositions containing an effective tumor-inhibiting amount of a compound of the present invention in combination with an inert pharmaceutically acceptable carrier or diluent. Such compositions may also contain other active antitumor agents and may be made up in any pharmaceutical form appropriate for the desired route of administration. Examples of such compositions include solid compositions for oral administration such as tablets, capsules, pills, powders and granules, liquid compositions for oral administration such as solutions, suspensions, syrups or elixirs and preparations for parenteral administration such as sterile solutions, suspensions or emulsions. They may also be manufactured in the form of sterile solid compositions which can be dissolved in sterile water, physiological saline or some other sterile injectable medium immediately before use.

For use as an antitumor agent, optimal dosages and regiments for a given mammalian host can be readily ascertained by those skilled in the art. It will, of course, be appreciated that the actual dose used will vary according to the particular compound selected, composition formulated, the route of administration and the particular situs, host and disease being treated. Many factors that modify the action of the drug will be taken into account including age, weight, sex, diet, time of administration, route of administration, rate of excretion, condition of the patient, drug combinations, reaction sensitivities and severity of the disease.

The following examples are illustrative of the invention and should not be construed as limiting the scope of the invention.

All temperatures are given in degrees Centigrade. Melting points were recorded on a Thomas-Hoover capillary melting point apparatus and are uncorrected. $^1$H NMR spectra were recorded either on a Bruker WM 360 or a Varian VX2 200 Spectrophotometer (using CDCl$_3$ as an internal reference). Chemical shifts are reported in δ units and coupling constants in Hertz. Splitting patterns are designated as follows: s, singlet; d, doublet; t, triplet; q, quartet; m, multiplet; bp, broad peak; and dd, doublet of doublet. Infrared spectra were determined either on a Beckman Model 4240 or a Perkin-Elmer 1800 Fourier Transform Infrared spectrophotometer and are reported in reciprocal centimeters. Thin-layer chromatography (TLC) was carried out on precoated silica gel plates (60F-254) using UV light and/or iodine vapors as visualizing agents. High and low resolution mass spectra were recorded on KRATOS MS 50 and KRATOS MS 25RFA Spectrophotometer respectively. "Flash Chromatography" refers to the method described by Still (Still W. C. et. al J. Org. Chem. 1978, 43, 2923) and was carried out using either E. Merck silica gel (200–400 mesh) or Woelm Silica gel (32–63μm). All evaporations of solvents were performed under reduced pressure.

EXAMPLE 1

Naphtho[2,3-d]-1,3-dioxole-6-carboxylic acid, 5,6,7,8-tetrahydro-8-[(4,6-0-ethylidene-8-D-glucopyranosyl) oxy]-5-[(4-hydroxy-3,5-dimethoxy)phenyl]-7-(hydroxymethyl)-, hydrazide, [5R-[5α,6α,7β,8β(R*)]]

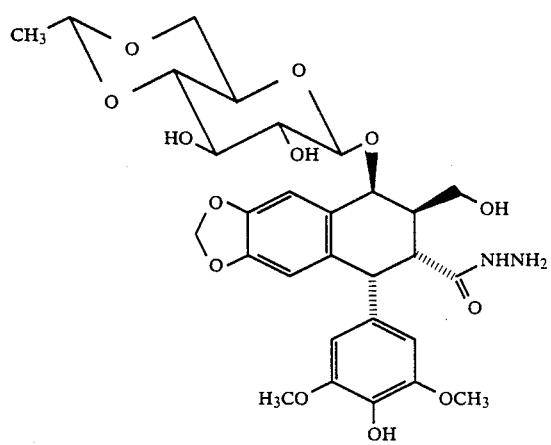

Glacial acetic acid (5 mL) followed by anhydrous hydrazine (5 mL) was added to a suspension of etoposide (5.1 g, 8.66 mmol) in methanol (50 mL). The resulting clear solution was refluxed for 2 h and during the second hour of reflux, a white precipitate formed. The reaction mixture was allowed to cool to room temperature and then filtered by suction (ethanol wash) to provide 2.20 g of a white solid which was mainly the cis hydrazide. Water (350 mL) was added to the filtrate and the mixture concentrated by rotary evaporation at 50° C. for 10 min. The aqueous solution was extracted with three 100 mL portions of 10% t-butanol in methylene chloride and kept in a refrigerator over night. The resultant precipitate was collected by filtration to provide 2.8 g (52%) of the desired trans hydrazide as a white solid: (occasionally the desired product will precipitate during this extraction and may be isolated by filtration.)

trans hydrazide

TLC rf=0.28 (20% methanol in methylene chloride).
IR (KBr) 3420,(b), 2950, 1738, 1665, 1620 cm$^{-1}$.
$^1$H NMR (CDCl$_3$) δ 8.19 (bs,1H, exchangeable) 6.58 (s,1H), 6.20 (bs,2H, 1 exchangeable) 5.95 (s,2H), 5.82 (s,2H), 4.91 (d,J=2.8Hz,1H), 4.54 (m,1H), 4.35 (bs,1H, exchangeable) 4.22 (d,J=7.6Hz,1H), 4.11 (d,J=6.8Hz,1H), 3.99 (dd,J=10.1,4.4Hz,1H), 3.55 (s,6H), 3.42-3.36 (m,3H), 3.15-3.08 (m,4H), 2.32 (m,1H), 1.16 (d,J=4.9Hz,3H).

cis hydrazide
TLC rf=0.44 (20% methanol in methylene chloride)
IR (KBr) 3340, 2910, 1661, 1615 cm$^{-1}$.
$^1$H NMR (DMSO-d6) δ 9.17 (bs,1H), 7.32 (s,1H), 6.27 (s,2H), 6.14 (s,1H), 5.85 (s,2H), 4.92 (m,1H), 4.73 (m,1H), 4.62 (d,J=9.5Hz,1H), 4.2 (m,2H), 4.0 (m,2H), 3.67 (s,6H), 3.70-3.40 (m,3H), 3.35-3.15 (m,3H), 2.97 (d,J=12.5Hz,1H), 2.42 (m,1H), 1.27 (d,J=5.8Hz,3H).

EXAMPLE 2

Naphtho[2,3-d]-1,3-dioxole-6-carboxamide, 5,6,7,8-tetrahydro-8-[(4,6-0-ethylidene-β-D-glucopyranosyl)oxy]-5-[(4-hydroxy-3,5-dimethoxy)-phenyl]-7-(hydroxymethyl)-, [5Rα,6α,7β,8β(R*)]-

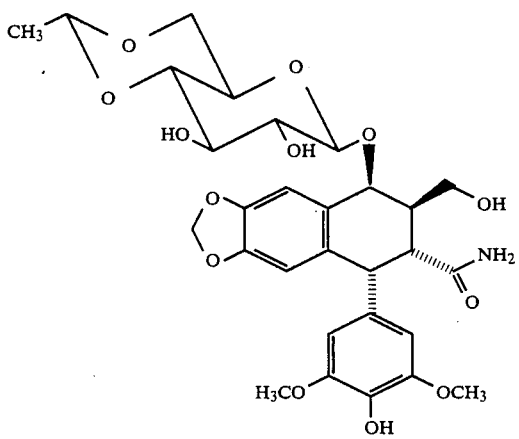

Raney nickel active catalyst (Aldrich, W2, 4 g) was washed three times with ethanol and added to a suspension of etoposide trans-hydroxy hydrazide [product of Example 1, 1.0 g, 1.61 mmol] in 5:1 ethanol in ethyl acetate (30 mL). The reaction mixture was refluxed for 3 h, stirred overnight at room temperature, and then filtered through celite with liberal ethanol in ethyl acetate washing to provide after concentration in-vacuo a light green solid. Flash chromatography on $SiO_2$ using 10% methanol in methylene chloride as eluent provided the title compound (0.60 g, 61%) as an off white solid.

IR (KBr) 3442, 2899, 1669, 1614, 1519, 1235 cm$^{-1}$.

$^1$H NMR (CDCl$_3$) δ 6.64 (s,1H), 6.41 (bs,1H), 6.31 (s,1H), 6.07 (s,2H), 5.83 (s,2H), 5.70 (bs,1H), 4.96 (d,J=2.7Hz,1H), 4.62 (q,J=4.7Hz,1H), 4.33 (d,J=7.2Hz,1H), 4.23 (d,J=6.4Hz,1H), 4.11–4.08 (m,1H), 3.69 (d,J=5.2Hz,2H), 3.62 (s,6H), 3.48 (t,J=9.04Hz,2H), 3.30 (m,1H), 3.21–3.15 (m,3H), 2.36 (m,1H), 1.26 (d,J=4.9Hz,3H).

EXAMPLE 3

6H-Pyrrolo[3',4':6,7]naphtho[2,3-d-1,3-dioxole-6-one,5-,5a,-7,8,8a,9-hexahydro-9-[(4,6-0-ethylidene-β-D-glucopyranosyl)oxy]-5-[(4-hydroxy-3,5-dimethoxy)phenyl]-7-[(phenylmethylene)amino]-, [5R-[5α,5aαβ,8aα,9β(R*)]A.

A. Naphtho[2,3-d]-1,3-dioxole-6-carboxylic acid, 5,6,7,8-tetrahydro-8-[(4,6-O-ethylidene-β-D-glucopyranosyl)oxy]-5-[(4-hydroxy-3,5-dimethoxy)-phenyl]-7-(hydroxymethyl)-, phenylmethylene hydrazide, [5R-[5α,6α,7β,8β(R*)]-

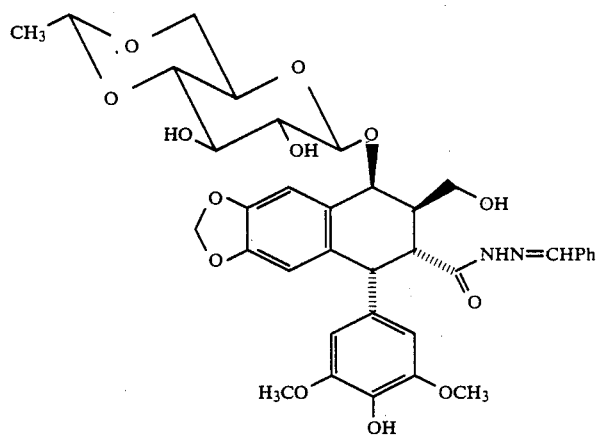

Benzaldehyde (1.0 mL, 9.84 mmol) was added to a stirred suspension of etoposide trans-hydroxy hydrazide (product of Example 1, 1.02 g, 1.64 mmol) in 12 mL of 2:1 methylene chloride/methanol at room temperature; after about 3 min. a clear yellow solution was obtained. TLC after 30 min showed nearly complete reaction and the formation of a single product (TLC rf=0.14; 5% methanol in methylene chloride). The reaction mixture was stirred for 15 h, concentrated in-vacuo, and then purified by flash chromatography on $SiO_2$ using methylene chloride, 5% methanol in methylene chloride, then 10% methanol in methylene chloride as eluent to provide the hydroxy hydrazone product (1.01 g, 87%) as a white solid.

IR (KBr) 3439, 2936, 2888, 1732, 1667, 1613, 1485 cm$^{-1}$.

FAB MS m/e (relative intensity) 709 (M+H).

$^1$H NMR (CDCl$_3$) (Complex isomer mixture) δ 8.84 (s, H), 7.44 (s, H), 7.16 (s, H), 7.13 (s, H), 6.99 (s, H), 6.79, 6.78 (s, H), 6.65 (s, H), 6.50 (s, H), 6.46 (s, H), 6.12 (s, H), 5.95 (m,2H), 5.56 (s, H), 4.95–4.85 (m, H), 4.72 (m,1H), 4.63–4.52 (m,2H), 4.41–4.35 (m,1H), 4.22–4.14 (m,2H), 4.0–3.85 (m,1H), 3.86, 3.76 (s,6H), 3.69 (m,1H), 3.55 (m,1H), 3.41 (m,1H), 3.32–3.21 (m, H), 2.89 (m,1H), 2.58, 2.24, 2.18, 2.09 (s,2H), 1.36 (d,4.9Hz,3H).

Anal. Calcd. for $C_{36}H_{40}N_2O_{13}$ (0.95% $H_2O$) C, 60.78; H, 5.68; N, 3.88. Found: C, 60.20; H, 5.73; N, 3.84.

B. 6H-Pyrrolo[3',4':6,7]naphtho[2,3-d]-1,3-dioxole-6-one, 5,5a,7,8,8a,9-hexahydro-9-[(4,6-O-ethylidene-β-D-glucopyranosyl)oxy]-5-[(4-hydroxy-3,5-dimethoxy)-phenyl]-7-[(phenylmethylene)amino][5R-[5α,5aβ,-8aα,9β(R*)]]-

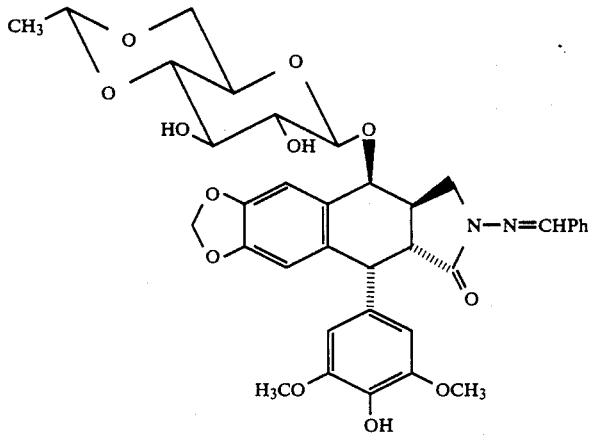

Diethylazodicarboxylate (0.89 mL, 5.62 mmol) was added over 2 min via syringe to a solution of the trans hydroxy hydrazone obtained in Step A above (2.1 g, 2.96 mmol) and triphenylphosphine (2.33 g, 8.88 mmol) stirring at 22° in 65 mL of dry THF under $N_2$. After 10 minutes the reaction mixture was poured into 125 mL of water and extracted with one 200 mL portion of 10% diethyl ether in ethyl acetate and then two 25 mL portions of methylene chloride. The combined organic layers were dried over anhydrous $MgSO_4$ and concentrated in-vacuo. Flash chromatography on $SiO_2$ using 4% then 5% methanol in methylene chloride as eluent provided several less polar by-products and then the desired title compound (1.85 g, 90%) as a white solid. TLC rf=0.26; (5% methanol in methylene chloride).

IR (KBr) 3443, 2918, 1726, 1649, 1613, 1231 cm$^{-1}$.
FAB MS m/e (relative intensity) 691 (M+H).

$^1$H NMR (CDCl$_3$) δ 7.70–6.64 (m,2H), 7.62 (s,1H), 7.37–7.35 (m,3H), 6.78 (s,1H), 6.55 (s,1H), 6.27 (s,2H), 5.99 (s,1H), 5.97 (s,1H), 5.36 (s,1H,4'OH), 4.99 (d,J=2.95Hz,1H), 4.76 (q,J=4.9,4.1Hz,1H), 4.69 (d,J=5.1Hz,1H), 4.61 (d,J=7.6Hz,1H), 4.25 (dd,J=10.2,3.6Hz,1H), 3.80–3.73 (m,1H), 3.73 (s,6H), 3.63–3.36 (m,7H), 2.79 (m,2H,1-OH), 1.39 (d,J=4.97Hz,3H).

$^{13}$C NMR (CDCl$_3$) 169.8, 148.5, 146.5, 146.3, 144.4, 133.9, 133.8, 133.6, 131.3, 130.1, 128.5, 127.6, 127.3, 111.2, 109.5, 108.1, 101.4, 99.9, 99.7, 79.9, 74.6, 73.1, 71.9, 68.2, 66.4, 56.5, 44.7, 44.2, 43.1, 32.8, 20.4.

Anal. Calcd. for $C_{36}H_{38}N_2O$ (0.83% $H_2O$) C, 62.00; H, 5.49; N, 3.76. Found: C, 61.50; H, 5.54; N, 3.73.

EXAMPLE 4

6H-Pyrrolo[3',4':6,7]naphtho[2,3-d]-1,3-dioxole-6-one, 5,5a,7,8,8a,9-hexahydro-9-[(4,6-O-ethylidene-β-D-glucopyranosyl)oxy]-5-[(4-hydroxy-3,5-dimethoxy)-phenyl]-7-[(phenylmethyl)amino]-, [5R-[5α,5aβ,-8aα,9β(R*)]]-

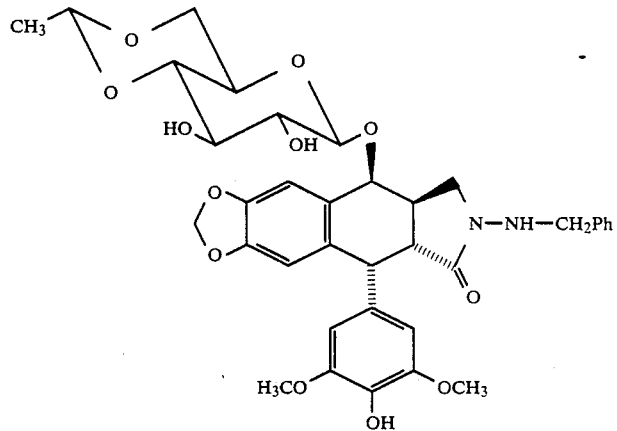

A solution of etoposide lactam benzyl hydrazone (product of Example 3, Step B, 0.20 g, 0.290 mmol) in 100 mL of MeOH containing 0.203 g of 10% palladium on carbon was hydrogenated at 50 PSI on a Parr shaker for 3.1 h. The reaction mixture was filtered through celite and concentrated in-vacuo. Flash chromatography on $SiO_2$ using 4% then 5% methanol as eluent provided the title compound (0.116 g, 55%) as a white solid.

IR (KBr) 3444, 2903, 1729(w), 1680, 1485, 1232 cm$^{-1}$.

$^1$H NMR (CDCl$_3$) δ 7.10 (m,3H), 6.89 (m,2H), 6.73 (s,1H), 6.45 (s,1H), 6.22 (s,2H), 5.91 (s,1H), 5.87 (s,1H), 5.67 (s,1H), 4.69 (m,2H), 4.53–4.47 (m,2H), 4.05 (m,1H), 3.76 (s, H), 3.70 (s,6H), 3.60 (t,J=8.69Hz,1H), 3.47 (t,J=9.70Hz,1H), 3.37 (t,J=9.0Hz,1H), 3.12-3.07 (m, H), 3.10 (dd,J=12.8,5.0Hz,1H), 2.68 (t,J=10.0Hz,1H), 2.33 (m,1H), 1.32 (d,J=4.9Hz,3H).

FAB MS m/e (relative intensity) 693 (M+H).

Anal. Calcd. for $C_{36}H_{40}N_2O_{12}$ (0.29% H20) C, 60.31; H, 5.70; N, 3.61. Found: C, 60.41; H, 5.72; N, 3.60.

EXAMPLE 5

6H-Pyrrolo[3',4':6,7]naphtho[2,3-d]-1,3-dioxole-6-one,5,5a,7,8,8a,9-hexahydro-9-[(4,6-O-ethylidene-β-D-glucopyranosyl) oxy]-5-[(4-hydroxy-3,5-dimethoxy)-phenyl]-, [5R-[5α,5aα,8aα, 9β(R*)]-

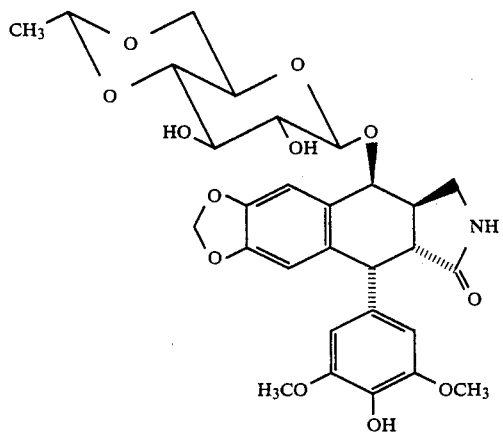

fraction 2 at 50° C./1 torr and flash chromatography provided an additional 0.164 g of the title compound (total yield 68%).

Anal. Calcd. for $C_{29}H_{33}NO_{12}$: C, 59.27; H, 5.66; N, 2.39. Found: C, 59.06; H, 5.81; N, 2.23.

IR (KBr) 3406, 2902, 1690, 1615, 1486 cm$^{-1}$.

$^{13}$C NMR (DMSO-d6) δ 174.8, 147.4, 146.8, 145.9, 134.2, 133.1, 131.0, 129.7, 109.8, 109.7, 108.4, 101.6, 101.0, 80.1, 79.5, 74.4, 72.8, 67.4, 65.6, 55.8, 43.6, 42.4, 40.7, 36.5, 20.2.

$^1$H NMR (DMSO-d6) δ 6.97 (s,1H), 6.48 (s,1H), 6.20 (s,2H), 5.98 (d,J=4.7Hz,2H), 4.84 (d,J=3.4Hz,1H), 4.69 (q,J=4.96,4.86Hz,1H), 4.58 (d,J=4.42,1H), 4.05 (q,J=5.08,4.7Hz,1H), 3.58 (s,6H), 3.49-3.43(m,2H), 3.35 (t,J=8.9Hz,2H), 3.23 (m,1H), 3.14 (t,J=9.4Hz,1H), 3.07-2.17 (m,2H), 2.92 (q,J=6.7,5.1Hz,1H), 2.58-2.48 (m,1H), 1.23 (d,J=4.86Hz,3H).

FAB MS m/e (relative intensity) 588 (M+H).

EXAMPLE 6

6H-Pyrrolo[3',4':6,7]naphtho[2,3-d]-1,3-dioxole-6-one, 5,-5a,7,8,8a,9-hexahydro-9-[(4,6-O-ethylidene-δ-D-glucopyranosyl)oxy]-5-[(4-hydroxy-3,5-dimethoxy)-phenyl]-7-[[(4-nitrophenyl)methylene]amino], [5R-[5α,5aβ,8aα,9β(R*)]-

A. Naphtho[2,3-d]-1,3-dioxole-6-carboxylic acid, 5,6,7,8-tetrahydro-8-[(4,6-O-ethylidene-β-D-glucopyranosyl)oxy]-5-[(4-hydroxy-3,5-dimethoxy)-phenyl]-7-(hydroxymethyl)-, (4-nitrophenyl)methylene hydrazide, [5R-[5α,6α,7β,8β(R*)]-

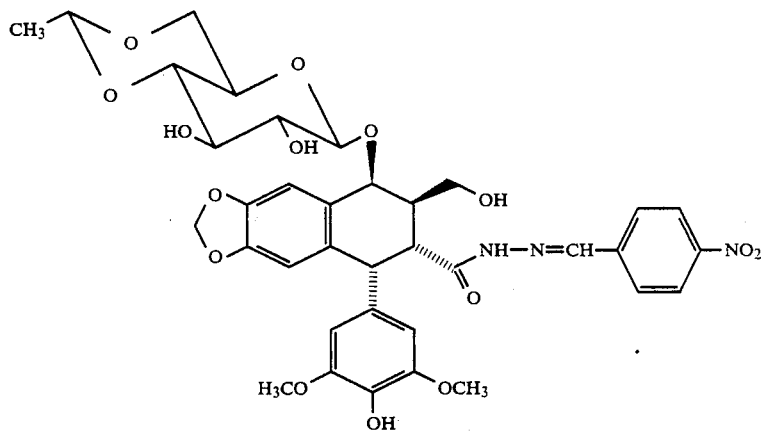

Five spoonulas of Raney nickel (Aldrich, W2) that had been washed to neutrality with water then ethanol was added to a solution of etoposide lactam benzyl hydrazone (product of Example 3, Step B, 0.74 g, 1.07 mmol) in 50 mL of absolute ethanol. The reaction mixture was refluxed for 3.5 h. Two mL of ethyl acetate and 1 more spoonula of Raney nickel was added. After refluxing for an additional 2.5 h the reaction mixture was filtered through a pad of celite using ethyl acetate as eluent to give fraction one. The reaction flask and the celite pad were rinsed with 150 mL of hot (≈80° C.) dimethylformamide to give a second fraction. Concentration of fraction one and flash chromatography on silica gel using 4 then 5% methanol in methylene chloride as eluent provided 0.107 g (14%) of the faster eluting, partially reduced product of Example 5 and 0.269 g of the title compound as a white solid. Concentration of The procedure of Example 3, Step A was followed using p-nitrobenzaldehyde rather than benzaldehyde to provide an 89% yield of the trans hydroxy hydrazone product as a light orange solid.

IR (KBr) 3443, 2925, 1732, 1683, 1345, 1235 cm$^{-1}$.

FAB MS m/e (relative intensity) 754 (M+H).

$^1$H NMR (CDCl$_3$) δ 10.8, 10.5 (s,1H), (ratio 3'1), 8.2 (m,2H), 7.96 (s,1H), 7.80 (m,2H), 6.79, 6.77 (s,1H), 6.44, 6.40 (s,1H), 6.11, 6.07 (s,2H), 5.93 (m,2H), 5.62, 5.54 (s,1H), 5.12 (bs,1H), 4.75 (m,1H), 4.60-4.17 (m,5H), 3.70, 3.66 (s,6H), 3.95-3.25 (m,4H), 2.59 (m,1H), 1.38 (d,J=8.6Hz,3H).

B. 6H-Pyrrolo[3',4':6,7]naphtho[2,3-d]-1,3-dioxole-6-one, 5,5a,7,8,8a,9-hexahydro-9-[(4,6-O-ethylidene-δ-D-glucopyranosyl)oxy]-5-[(4-hydroxy-3,5-dimethoxy)-phenyl]-7-[[(4-nitrophenyl)methylene]amino], [5R-[5α,-5aβ,8aα,9β(R*)]-

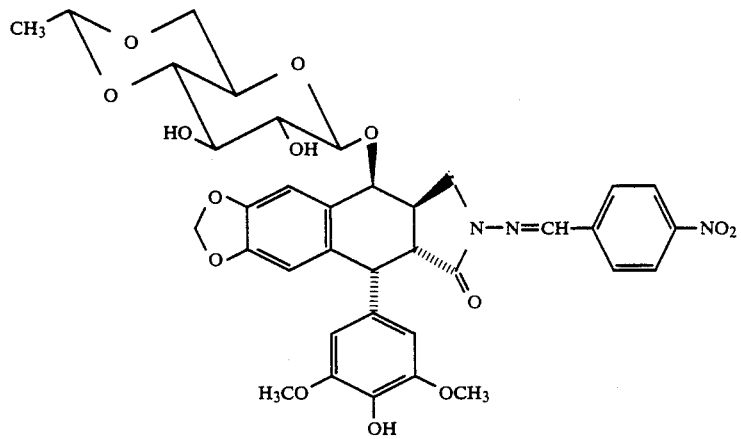

The procedure of Example 3, Step B was followed using as starting material the trans hydroxy hydrazone prepared in Step A above to provide the title compound in 78% yield as a light yellow powder.

IR (KBr) 3475, 2900, 1721, 1611, 1600, 1519, 1486 cm$^{-1}$.

FAB MS m/e (relative intensity) 736 (M+H).

$^1$H NMR (CDCl$_3$ δ 8.20 (d,J=8.7Hz,2H), 7.85 (m,3H), 6.80 (s,1H), 6.56 (s,1H), 6.30 (s,2H), 5.99 (d,9.7Hz,2H), 5.37 (s,4'OH), 5.01 (d,J=3.06Hz,1H), 4.78–4.71 (m,2H), 4.67 (d,J=7.8Hz,1H), 4.24 (dd,J=10.3,3.78Hz,1H), 3.85 (t,J=9.6Hz,1H), 3.76 (s,6H), 3.76–3.55 (m,3H), 3.51–3.32 (m,5H), 2.90–2.81 (m,1H), 2.65 (s,sug-OH), 2.39 (s,sug-OH), 1.39 (d,J=4.9Hz,3H).

Anal. Calcd. for C$_{36}$H$_{37}$N$_3$O$_{14}$: 0.8% H20: C, 58.47; H, 5.09; N, 5.39. Found: C, 58.00; H, 5.14; N, 5.35.

EXAMPLE 7

6H-Pyrrolo[3',4':6,7]naphtho[2,3-d]-1,3-dioxole-6-one, 5,5a,7,8,8a,9-hexahydro-7-amino-9-[(4,6-O-ethylidene-β-D glucopyranosyl)oxy]-5-[(4-hydroxy-3,5-dimethoxy)-phenyl]-, [5R-[5α,5aβ,8aα,9β(R*)]]-

A. Naphtho[2,3-d]-1,3-dioxole-6-carboxylic acid, 5,6,7,8-tetrahydro-8-[(4,6-O-ethylidene-β-D-glucopyranosyl)oxy]-5-[(4-hydroxy-3,5-dimethoxy)-phenyl]-7-(hydroxymethyl)-, 2-propylidene hydrazide, [5R-[5α,6α,7β,8β(R*)]]-

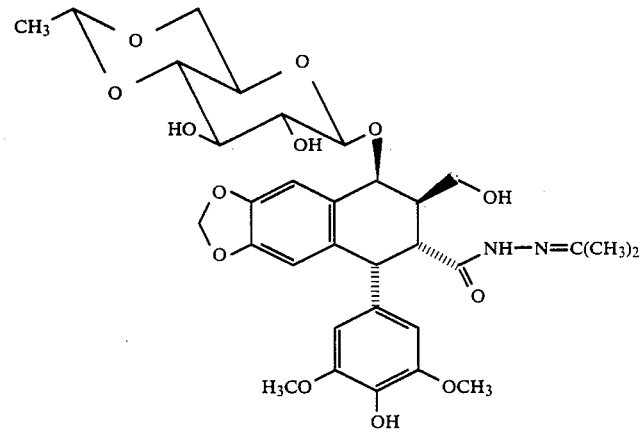

A suspension of etoposide trans hydroxy hydrazide (product of Example 1, 3.39 g, 5.46 mmol) in 150 mL of acetone was refluxed for 1 h. The reaction mixture was cooled to room temperature and concentrated in-vacuo. Flash chromatography on SiO$_2$ using 5% methanol in methylene chloride then 10% methanol in methylene chloride as eluent provided the less polar desired product (2.53 g, 70%) as a white solid.

IR (KBr) 3423, 2939, 2905, 1667, 1616, 1519, 1486 cm$^{-1}$ $^1$H NMR (CDCl$_3$/DMSO-d6) δ 8.85, 8.70 (1H), 6.55, 6.64 (s,1H), 6.29, 6.24 (s,1H), 6.00, 5.99, 5.92 (s,2H), 5.78–5.75 (m,2H), 4.96 (m,1H),4.59 (m,1H), 4.47 (d,J=7.82Hz,0.4H), 4.34–4.03 (m,3.6H), 3.59, 3.57 (s,6H), 3.64–3.16 (m,8H), 2.51–2.43 (m,5H), 1.88, 1.86, 1.82, 1.70 (s,6H), 1.23 (d,J=5.0Hz,3H).

B. O+N Cyclized products of N-isopropylidene etoposide trans hydroxy hydrazide

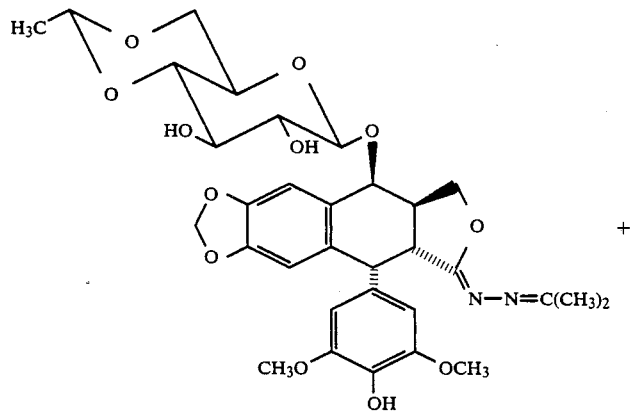

Diethylazodicarboxylate (0.205 mL, 1.29 mmol) was added to a solution of triphenylphosphine (0.567 g, 2.16 mmol) and the trans hydroxy hydrazone product of Step A above (0.47 g, 0.72 mmol) stirring at room temperature in 16 mL of dry tetrahydrofuran. The reaction mixture was stirred for 10 min and poured into 90 mL of ethyl acetate and 30 mL of water. The organic layer was separated, dried over $MgSO_4$, concentrated in-vacuo and purified by flash chromatography on $SiO_2$ using 4% methanol in methylene chloride as eluent to provide a mixture of O and N cyclized materials (0.260 g, 57%) as a tan solid.

$^1H$ NMR ($CDCl_3$) δ 6.80, 6.79 (s,1H), 6.50, 6.47 (s,1H), 6.27, 6.22 (s,2H), 5.93–5.89 (m,2H), 5.48 (m,4'OH), 4.97 (m,1H), 4.70 (m,1H), 4.59–4.50 (m,2H), 4.37 (t,J=12.0Hz,0.3H), 4.23 (t,J=11.8Hz,0.3H), 4.12 (m,2H), 4.01 (t,J-12.0Hz,0.7H), 3.68, 3.67 (s,6H), 3.80–3.20 (m,7H), 3.85, 2.57 (bm,1H), 2.01, 1.90, 1.85, 1.52 (s,6H), 1.34 (d,J=5.0Hz,3H).

C. 6H-Pyrrolo[3',4':6,7]naphtho[2,3-d]-1,3-dioxole-6-one, 5,5a,7,8,8a,9-hexahydro-7-amino-9-[(4,6-O-ethylidene-β-D-glucopyranosyl)oxy]-5-[(4-hydroxy-3,5-dimethoxy)phenyl]-, [5R-[5α,5aβ,8aα,9β(R*)]-

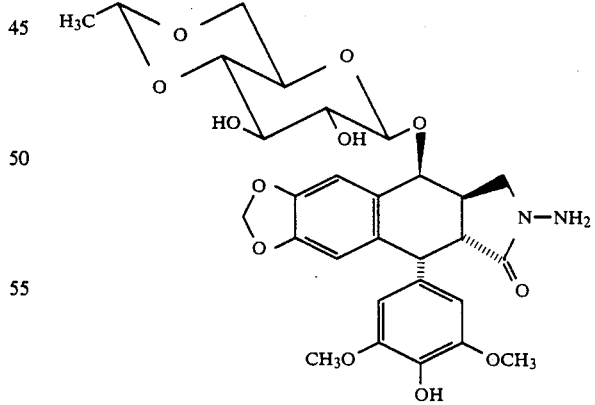

A mixture of O+N cyclized products of Step B above (0.91 g, 1.43 mmol) was suspended in $CH_2Cl_2$ and methanol was added until the solid dissolved. The solution was allowed to stand open in the air until evaporated to dryness. This procedure was repeated every 3 or 4 days for 3 weeks. Purification using medium pressure chromatography on $SiO_2$ using 8% $MeOH/CH_2Cl_2$ then 10% $MeOH/CH_2Cl_2$ as eluent provided 0.470 g of recovered starting materials and 0.20 g (23%) of the slower eluting desired title compound as a cream colored solid:

FAB MS m/e (relative intensity) 603 (M+H)+.
IR (KBr) 3420, 2910, 1680, 1618, 1485 cm$^{-1}$.
$^1$H NMR (CDCl$_3$) δ 6.79 (s,1H), 6.51 (s,1H), 6.25 (s,2H), 5.95 (d,J=12.1Hz,2H), 5.44 (bs,4'-OH), 4.86 (d,J=3.0Hz, 1H), 4.72 (m,1H), 4.61–4.57 (m,2H), 4.14 (dd,J=11.3,4.1Hz,1H), 3.97 (bs,2H), 3.72 (s,6H), 3.72–3.54 (m,2H), 3.40 (t,J=8.2Hz,1H), 3.32–3.25 (m,3H), 3.14 (dd,J=12.9,5.1Hz,1H), 2.95 (bs,sugar-OH), 2.78 (bs,sugar-OH), 2.57 (m,1H), 1.37 (d,J=5.0Hz,3H).

EXAMPLE 8

6H-Pyrrolo[3',4':6,7]naphtho[2,3-d]-1,3-dioxole-6-one, 5,5,a,7,8,8a,9-hexahydro-9-[(4,6-O-ethylidene-β-D-glucopyranosyl)oxy]-5-[(4-hydroxy-3,5-dimethoxy)-phenyl]-7-[(2-propylidene)amino]-, IR (KBr) 3450, 2902, 1688, 1613, 1231, 1116 cm
$^1$H NMR (CDCl$_3$) δ 6.85 (s,1H), 6.58 (s,1H), 6.31 (s,2H), 6.00 (d,J=4.4Hz,2H), 5.41 (bs,4'-OH), 4.97 (m,1H), 4.77 (q,J=4.4Hz,1H), 4.68–4.61 (m,2H), 4.17 (dd,J=10.8,3.6Hz,1H), 4.01 (t,J=12.0Hz,1H), 3.76 (s,6H), 3.80–3.42 (m,3H), 3.40–3.21 (m,4H), 2.68 (m,1H), 2.07 (s,3H), 1.59 (s,3H), 1.41 (d,J-5.0Hz,3H).

EXAMPLE 9

6H-Pyrrolo[3',4':6,7]naphtho[2,3-d]-1,3-dioxole-6-one, 5,5,a,7,8,8a,9-hexahydro-9-[(4,6-O-ethylidene-β-D-glucopyranosyl)oxy]-5-[(4-hydroxy-3,5-dimethoxy)-phenyl]-7-[(octylidene)amino]-,
[5R-[5α,5aβ,8aα,9β(R*)]-

A. Naphtho[2,3-d]-1,3-dioxole-6-carboxylic acid, 5,6,7,8-tetrahydro-8-[(4,6-O-ethylidene-β-D-glucopyranosyl)oxy]-5-[(4-hydroxy-3,5-dimethoxy)-phenyl]-7-(hydroxymethyl)-, octylidene hydrazide, [5R-[5α,6α,7β,8β(R*)]-

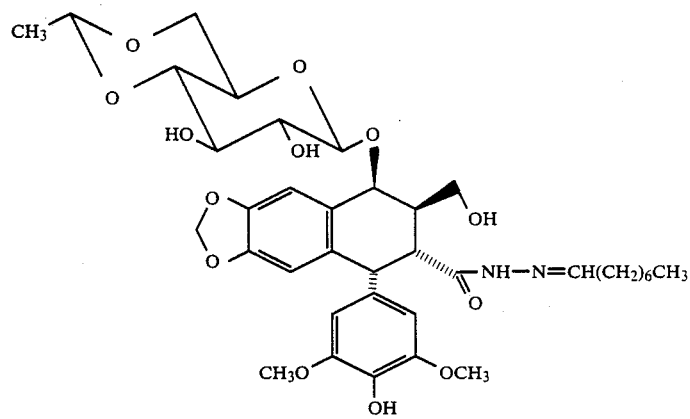

Octylaldehyde (1 mL, 9.5 mmol) followed by pyri-

[5R-[5α,5aβ,8aα,9β(R*)]-

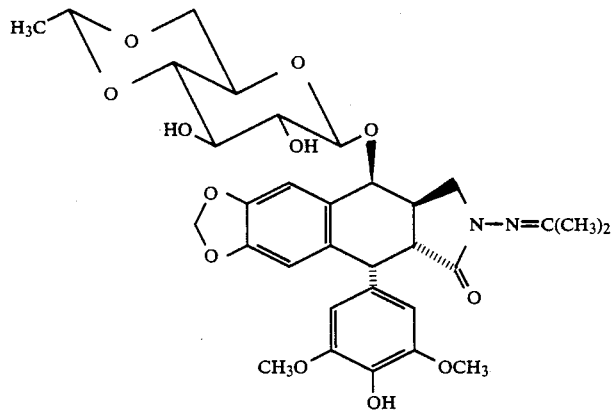

Etoposide lactam hydrazide (product of Example 7, Step C; 0.35 mg, 0.06 mmol) was dissolved in 15 mL of HPLC grade acetone and refluxed for 15 minutes TLC showed complete formation of a single new less polar product (10% MeOH/CH$_2$Cl$_2$ eluent). The solution was stirred for 14h at room temperature and then concentrated in-vacuo to provide 37 mg of crude product. Flash chromatography over SiO$_2$ using 10% MeOH/CH$_2$Cl$_2$ as eluent provided 33 mg (91%) of the title compound as cream colored solid:

FAB MS m/e (relative intensity) 643 (M+H).

dinium p-toluene sulfonate (10 mg) was added to a solution of etoposide trans hydroxy hydrazide (product of Example 1, 1.0 g, 1.60 mmol) in 25 mL of dichloromethane stirring at room temperature under N$_2$. The reaction mixture was stirred for 18 h, concentrated in-vacuo, and then flash chromatographed using methylene chloride, 5% methanol in methylene chloride, then 10% methanol in methylene chloride as eluent on SiO$_2$ to give the desired hydrazone product (TLC rf=0.05;

5% methanol in methylene chloride) as a white solid (0.537 g, 46%).

$^1$H NMR (CDCl$_3$) δ 9.50 (bs,1H), 8.74, 8.47 (s,1H), 7.17 (m,1H), 6.82, 6.80 (s,1H), 6.45 (s,1H), 2.10, 2.09 (s,2H), 5.95 (bs,2H), 5.50 (m,1H), 5.05 (m,1H), 4.75 (m,1H), 4.65 (d,10.0Hz,1H), 4.50–4.30 (m,3H), 4.25–4.00 (m,2H), 3.75 (s,1H), 3.90–3.10 (m,10H), 2.40–2.05 (m,5H), 1.70–1.05 (m,15H), 0.89 (m,3H).

B. 6H-Pyrrolo[3',4':6,7]naphtho[2,3-d]-1,3-dioxole-6-one, 5,5a,7,8,8a,9-hexahydro-9-[(4,6-O-ethylidene-β-D-glucopyranosyl)oxy]-5-[(4-hydroxy-3,5-dimethoxy)-phenyl]-7-[(octylidene)amino]-, [5R-[5α,5aβ,8aα,9β(R*)]-

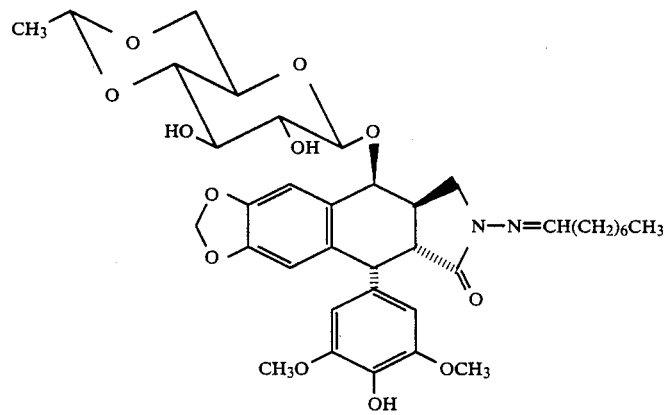

Diethylazodicarboxylate (0.19 mL, 1.2 mmol) was added dropwise to a solution of triphenyl phosphine (0.538 g, 2.05 mmol) and the hydrazone product of step A above (0.50 g, 0.684 mmol) in 15 mL of dry tetrahydrofuran stirring at room temperature under N$_2$. TLC (5% methanol in methylene chloride) after 20 min showed complete consumption of starting material and the formation of several new, less polar products. The reaction mixture was poured into 100 mL water and extracted with 150 mL portion of ethyl acetate and then one 20 mL portion of ethyl acetate. The combined organic layers were dried over anhydrous MgSO$_4$, concentrated in-vacuo and then purified by flash chromatography on SiO$_2$ using 3% then 5% methanol in methylene chloride as eluent to provide the title compound (0.244 g, 50%) as a white solid.

FAB MS m/e (relative intensity) 713 (M+H).
IR (KBr) 3460, 2928, 2872, 2858, 1713, 1615, 1486, 1116 cm$^{-1}$.
$^1$H NMR (CDCl$_3$) δ 7.10 (t,J=5.4Hz,1H), 6.83 (s,1H), 6.59 (s,1H), 6.33 (s,2H), 6.01 (d,J=6.0Hz,2H), 5.43 (bs,4'—OH), 4.97 (d,J=2.6Hz,2H), 4.97–4.65 (m,3H), 4.21 (dd,J=10.2,3.6Hz,1H), 3.77 (s,6H), 3.78–3.50 (m,4H), 3.47–3.31 (m,5H), 2.80–2.66 (m,3H), 2.35 (m,2H), 1.50–1.29 (m,10H), 1.42 (d,J=5.0Hz,3H), 0.89 (t,J=13.2Hz,3H).

EXAMPLE 10

6H-Pyrrolo[3',4':6,7]naphtho[2,3-d]-1,3-dioxole-6-one, 5,5a,7,8,8a,9-hexahydro-9-[(4,6-O-ethylidene-β-D-glucopyranosyl)oxy]-5-[(3,5-dimethoxy-4-octanoyl oxy)phenyl]-7-[(phenylmethylene)amino]-, [5R-[5α,5aβ,8aα,9β(R*)]-

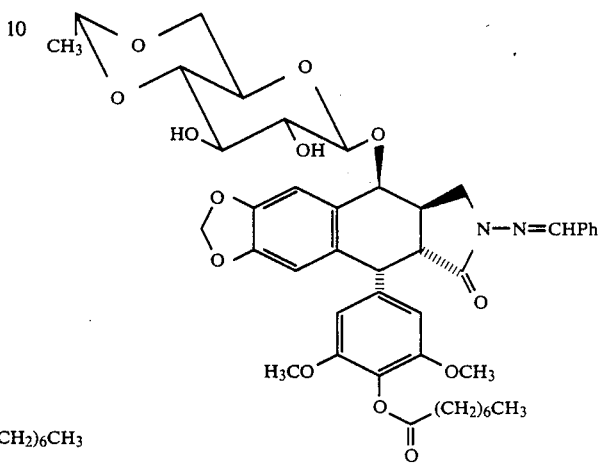

Octanoyl chloride (0.122 mL, 0.71 mmol) was added dropwise to a solution of etoposide lactam benzyl hydrazone (product of Example 3, Step B, 0.450 g, 0.65 mmol) and diisopropyl ethyl amine (0.169 mL, 0.975 mmol) stirring at room temperature in 10 mL of acetonitrile under N$_2$. After 30 min TLC (5% methanol in methylene chloride) showed the formation of a new less polar product and the consumption of starting material. The reaction mixture was poured into 25 mL of water and extracted with three 50 mL portions of ethyl acetate. The combined organic layers were dried over MgSO$_4$, concentrated in-vacuo and purified by flash chromatography on SiO$_2$ using 4% then 5% methanol in methylene chloride as eluent to provide the title compound (299 mg, 56%) as a white solid.

FAB MS m/e (relative intensity) 817 (M+H).
IR (KBr) 3441, 2991, 2918, 1699, 1669, 1628, 1234 cm$^{-1}$.
$^1$H NMR (CDCl$_3$) δ 7.67–7.62 (m,2H), 7.62 (s,1H), 7.36–7.35 (m,3HO, 6.78 (s,1H), 6.57 (s,1H), 6.28 (s,2H), 5.98 (d,J=6.0Hz,2H), 4.98 (d,J=2.9Hz,1H), 4.76 (m,1H), 4.72 (d,J=5.08Hz,1H), 4.60 (d,J=7.6Hz,1H), 4.25 (dd,J=10.2,3.7Hz,1H), 3.80 (t,J=9.4Hz,1H), 3.72 (t,J=8.5Hz,1H), 3.64 (s,6H), 3.60–3.45 (m,4H), 3.38–3.36 (m,2H), 2.76–2.73 (m,1H), 2.52 (t,J=7.4Hz,2H), 1.17–1.64 (m,2H), 1.39 (d,J=4.9Hz,3H), 1.39–1.22 (m,8H), 0.84 (t,J=6.3Hz,3H).

EXAMPLE 11

6H-Pyrrolo[3′,4′:6,7]naphtho[2,3-d]-1,3-dioxole-6-one, 5,5a,7,8,8a,9-hexahydro-9[(4,6-O-ethylidene-β-D-glucopyranosyl)oxy]-5-[(3,5-dimethoxy-4-octanoyl oxy)phenyl], [5R-[5α,5aβ,8aα,9β(R*)]-

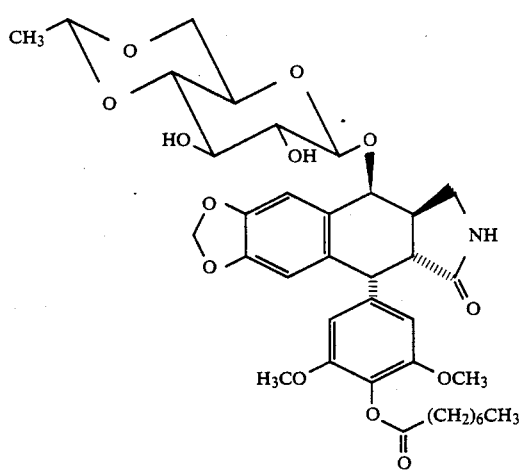

Three scoopulas of Raney nickel (W-2, washed to neutrality) was added to a stirred solution of etoposide lactam benzyl hydrazone octyl ester (product of Example 10, 0.20 g, 0.245 mmol) in 15 mL of ethanol. The reaction mixture was refluxed for 2.3 h. An additional scoopula of Raney nickel was added and the reaction mixture was refluxed for an additional 1.5 h. The reaction mixture was allowed to cool to room temperature, filtered through celite, and the filtrate was concentrated in-vacuo. Flash chromatography on SiO2 using 4% methanol in methylene chloride as eluent provided 0.121 g (69%) of the title compound as an off-white powder.

$^1$H NMR (CDCl3) δ 6.85 (s,1H), 6.57 (s,1H), 6.31 (s,2H), 5.99 (d,J=12.2Hz,2H), 4.91 (d,J=2.9Hz,1H), 4.79 (m,1H), 4.67 (m,2H), 4.22 (dd,J=10.2,3.7Hz,1H), 3.69 (s,6H), 3.75–3.50 (m,2H), 3.50–3.25 (m,4H), 3.20–3.05(m,2H), 2.76–2.73 (m,1H), 2.62 (t,J=7.5Hz,2H), 1.8–1.55 (m,2H), 1.39 (d,J=4.9Hz,3H), 1.39–1.20 (m,8H), 0.84 (t,J=6.2Hz,3H).

EXAMPLE 12

Naphtho,[2,3-d]-1,3-dioxole-6-carbonitrile, 5,6,7,8-tetrahydro-8-[(4,6-O-ethylidene-β-D-glucopyranosyl)oxy]-5-[(4-hydroxy-3,5-dimethoxy)-phenyl]-7-(hydroxymethyl)-,[5R-[5α,6α,7β,8β(R*)]-

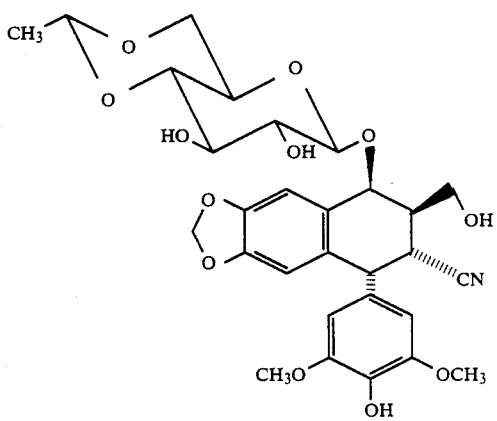

p-Toluene sulfonyl chloride (35 mg, 0.18 mmol) was added to a solution of etoposide hydroxy amide (product of Example 2, 100 mg, 0.165 mmol) in pyridine (2 mL) stirring at 2° C. under N2. The solution was stirred for an additional 5 minutes and then refrigerated at 3° C. for 16h. The solution was then concentrated in-vacuo and the residue flash chromatographed over SiO2 using 5% MeOH/CH2Cl2. The first eluting fractions contained 31 mg of an unidentified tosylation product. The slower eluting product was the desired hydroxy nitrile and was isolated as a white amorphous solid (51 mg, 53%):

FAB MS m/e (relative intensity) 587 (M+).

IR (KBr) 3475, 3070, 2992, 2240, 1615 cm$^{-1}$.

$^1$H NMR (CDCl3) δ 6.78 (s,1H), 6.42 (s,1H), 6.20 (s,2H), 5.95 (m,2H), 5.49 (bs,4′-OH), 5.00 (d,J=3.2Hz,1H), 4.73 (m,1H), 4.70 (d,J=7.7Hz,1H), 4.31 (d,J=5.6Hz,1H), 4.18 (dd,J=10.3,5.6Hz,1H), 4.83–3.71 (m,2H), 3.77 (s,6H), 3.61–3.51 (m,2H), 3.44–3.32 (m,3H), 2.47 (m,1H), 1.36 (d,J=4.3Hz,3H).

$^{13}$C NMR (CDCl3) 148.7, 146.9, 146.7, 134.6, 130.74, 130.54, 126.6, 119.3, 109.9, 108.4, 107.2, 101.5, 101.3, 99.8, 79.6, 74.3, 74.2, 73.1, 67.8, 66.7, 61.2, 58.5, 45.6, 38.1, 31.1, 20.3.

EXAMPLE 13

6H-Pyrrolo[3',4':6,7]naphtho[2,3-d]1,3-dioxole-6one, 5,5a,7,8,8a,9-hexahydro-9-[4,6-O-ethylidene-β-Dglucopyranosyl)oxy]-5-[(3,5-dimethoxy-4-diphenylphosphonooxy)phenyl]-7-[(phenylmethylene)amino]-, [5R-[5α,5aβ, 8aα,9β(R*)]-

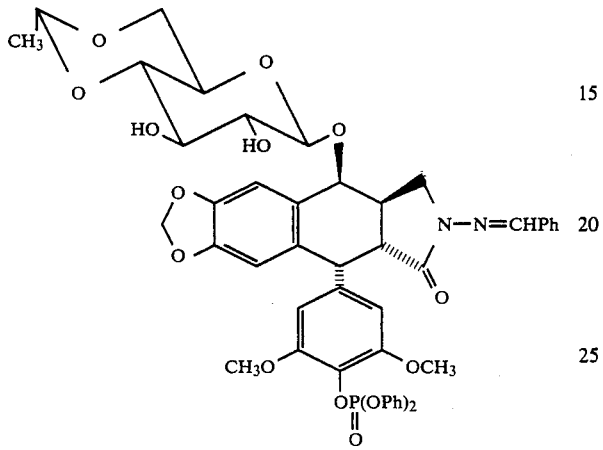

Etoposide lactam benzyl hydrazone (product of Example 3, 2.36 g, 3.42 mmol) was dried at 85° C. and 0.2 mm vacuum for 7 h and after cooling was dissolved in 45 ml of acetonitrile under nitrogen atomosphere. To this solution was added diisopropylethylamine (0.89 mL, 5.1 mmol) via syringe followed by diphenylchlorophosphate (0.88 mL, 4.27 mmol). The reaction vessel was placed in an oil bath maintained at 40–45° C. and the reaction mixture was stirred for 25 h and then poured into 100 mL of water. The organic solvent was removed by rotary evaporation and the aqueous layer was extracted with 100 mL and then 40 mL of methylene chloride. The combined organic extracts were dried over anhydrous sodium sulfate and then flash chromatographed on $SiO_2$ using 3%, 4%, and then 5% methanol in methylene chloride to provide the desired title compound (2.015 g, 64%) as a white solid.

M.P. 175°–180° C.

IR (KBr) 3442, 2893, 1705, 1601, 1487 $cm^{-1}$

FAB MS, m/e 923[M+923.2782 ($C_{48}H_{47}N_2O_{15}P$ requires 923.2792)]

$^1$H NMR ($CDCl_3$) δ 7.67–7.63 (m, 2H) 7.37–7.35 (m, 2H) 7.31–7.26 (m, 10H) 7.14 (bm, 2H) 6.77 (s, 1H) 6.52 (S, 1H) 6.23 (s, 2H) 5.97 (sharp m, 2H) 4.95 (d, J=3.0 Hz, 1H) 4.75 (m, 1H) 4.68 (d, J=5.1Hz, 1H) 4.60 (d, J=7.7Hz, 1H) 4.23 (dd, J=10.0, 3.2Hz, 1H) 3.82–3.52 (m, 5H) 3.49 (s, 6H) 3.45 (m, 1H) 3.36 (m, 2H) 3.24 (m, sugar-OH) 2.80 (m, sugar-OH) 2.72 (bm, 1H) 1.38 (d, J=4.6Hz, 3H)

EXAMPLE 14

6H-Pyrrolo[3',4':6,7]naphtho[2,3-d]1,3-dioxole-6-one, 5,5a,7,8,8a,9-hexahydro-9-[4,6-O-ethylidene-β-D-glucopyranosyl)oxy]-5-[(3,5-dimethoxy-4-diphenyl-phosphonooxy)phenyl]-, [5R-[5α,5β,8aα,9β(R*)]-

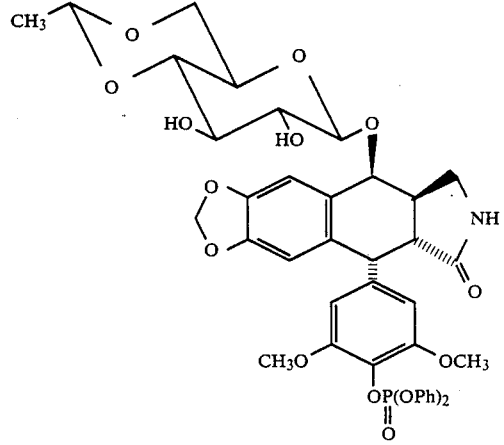

The product of example 13 (1.4 g, 1.52 mmol) was dissolved in 40 ml of absolute ethanol. Approximately 10 spoonulas of Raney Nickel (W-2) which had been previously washed to neutrality with water was added and rinsed into the flask with 5 mL EtOH. The reaction mixture was refluxed for 3 h and then filtered through celite with ethanol and ethylacetate washing. TLC (10% $MeOH/CH_2Cl_2$ on $SiO_2$) of the filtrate showed the presence of two products more polar than the starting material. Flash chromatography on $SiO_2$ using 4% then 5% then 10% methanol in methylene chloride as eluent provided a faster eluting product (0.210 g, 17%) as an off white solid which was identified by $^1$H NMR as the partially reduced benzyl hydrazide. The slower eluting product (0.498 g, 40%) provided the title compound as a white solid:

M.P. 163°–165° C.

IR (KBr) 3426, 2902, 1690, 1601, 1487, 1191 $cm^{-1}$.

FAB MS m/e 820 [M+, 820.2350 ($C_{41}H_{42}NO_{15}P$ requires 820.2370)]

$^1$H NMR ($CDCl_3$) δ 7.33–7.29 (m, 8H) 7.17 (bm, 2H) 6.78 (1H) 6.49 (1H) 6.23 (2H) 5.33 (bs, 1H) 4.84 (d, J=3.3Hz, 1H) 4.72 (m, 1H) 4.62–4.57 (m, 2H) 4.16 (dd, J=10.2, 3.8Hz, 1H) 3.64 (t, J=8.4Hz, 1H) 3.55 (m, 1H) 3.49 (s, 6H) 3.40 (t, J=8.2Hz, 1H) 3.31 (m, 2H) 3.17–3.07 (m, 2H) 2.83 (bs, sugar-OH) 2.64 (m, 1H +sugar-OH) 1.37 (d, J=5.06Hz, 3H).

EXAMPLE 15

6H-Pyrrolo[3',4':6,7]naphtho[2,3-d]-1,3-dioxole-6-one, 5,5a,7,8,8a,9-hexahydro-9-[(4,6-O-ethylidene-β-Dglucopyranosyl)oxy]-5-[(3,5-dimethoxy-4-phosphonoxy)phenyl]-1, disodium salt, [5R-[5α,5aβ,8aα,9β(R*)]-

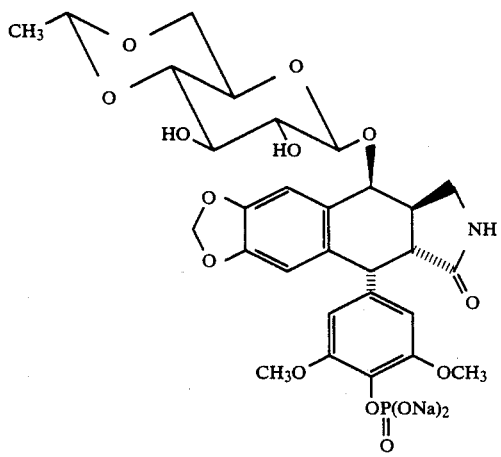

To a solution of the product of Example 14 10.44 g, 0.54 mmol) in aboslute ethanol (120 mL) was added crystalline PtO$_2$ (312 mg) and the mixture was hydrogenated in a Parr apparatus for 15 h at 60 psi and ambient temperature. The catalyst was removed by filtration through a pad of celite and the filtrate was concentrated by rotary evaporation to provide crude dihydrogen phosphate of the starting material. This crude product was dissolved in saturated aqueous sodium bicarbonate (45 ml) and flash chromatographed on a C$_{18}$ ODS column using water then 10% then 20% aqueous methanol as eluant to provide a U.V. visible fraction which was lyophilized for 48 h to provide the title compound (251.3 mg, 70%) as a white fluffy solid.

M.P. >250° C. slowly decomposes with heating above 250° C.

IR (KBr) 3440 (b), 2912, 1682, 1509, 1489 cm$^{-1}$.

FAB MS m/e relative intensity) M+H 712

$^1$H NMR (D$_2$O) δ 6.96 (s, 1H) 6.61 (s, 1H) 6.29 (s, 2H) 5.95 (d, J=4.6 Hz, 2H) 5.08 (d, J=2.7Hz, 1H) 4.88 (m, 1H, partially obscured by H$_2$O) 4.74 (d, J=9.3Hz, 1H) 4.61 (d, J=5.5Hz, 1H) 4.27 (dd, J=10.7, 4.6Hz, 1H) 3.70-3.26 (m, 8H) 3.66 (s, 6H) 3.00 (bm, 1H) 1.34 (d, J=5.0Hz, 3H)

EXAMPLE 16

The general procedure described in Examples 1 to Example 12 are repeated with the exception that etoposide or etoposide derivatives used therein is replaced by teniposide or the corresponding teniposide derivative to provide the corresponding teniposide products.

EXAMPLE 17

The procedure of Example 3, Step A is followed using the carbonyl compounds listed below to provide hydroxy hydrazones of formula XIII (wherein R$^1$ is H and R$^2$ is methyl). The hydroxy hydrazones thus obtained are cyclized using the procedure described in Example 3, Step B to give the corresponding lactam hydrazones of formula XIV.

| Carbonyl | Product of formulas XIII and XIV |
|---|---|
| phenylacetaldehyde | R$^5$=H; R$^6$=benzyl |
| p-anisaldehyde | R$^5$=H; R$^6$=p-methoxyphenyl |
| cyclohexanecarboxaldehyde | R$^5$=H; R$^6$=cyclohexyl |
| butyraldehyde | R$^5$=H; R$^6$=propyl |
| isovaleraldehyde | R$^5$=H; R$^6$=isobutyl |
| p-tolualdehyde | R$^5$=H; R$^6$=p-tolyl |
| p-hydroxybenzaldehyde | R$^5$=H; R$^6$=p-hydroxyphenyl |
| p-chlorobenzaldehyde | R$^5$=H; R$^6$=p-chlorophenyl |
| p-dimethylaminobenzaldehyde | R$^5$=H; R$^6$=p-dimethylaminophenyl |
| p-cyanobenzaldehyde | R$^5$=H; R$^6$=p-cyanophenyl |
| p-(methylthio)benzaldehyde | R$^5$=H; R$^6$=p-(methylthio)phenyl |
| 2-butanone | R$^5$=methyl; R$^6$=ethyl |
| methyl isobutyl ketone | R$^5$=methyl; R$^6$=isobutyl |
| 3-pentanone | R$^5$=ethyl; R$^6$=ethyl |
| acetophenone | R$^5$=methyl; R$^6$=phenyl |
| 4-pyridinecarboxaldehyde | R$^5$=H; R$^6$=4-pyridyl |
| 2-acetylpyrrole | R$^5$=methyl; R$^6$=pyrrolyl |
| benzophenone | R$^5$=R$^6$=phenyl |
| 1,3-dichloroacetone | R$^5$=R$^6$=chloromethyl |
| 4-chloro-3-nitrobenzaldehyde | R$^5$=H; R$^6$=4-chloro-3-nitrophenyl |
| (4-trifluoromethyl) benzophenone | R$^5$=phenyl; R$^6$=4-trifluoromethylphenyl |

What is claimed is

1. A compound having the formula

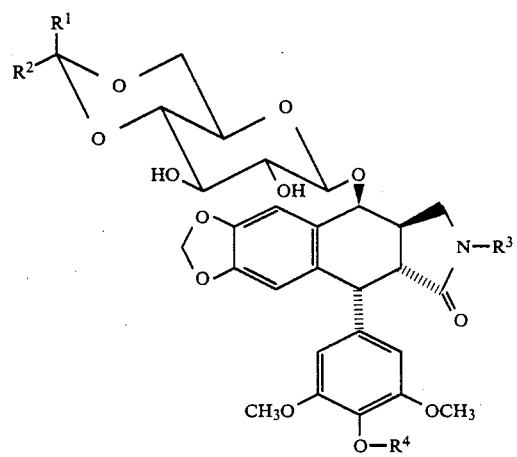

wherein

R$^1$ and R$^2$ are each C$_{1-10}$alkyl; or R$^1$, R$^2$, and the carbon to which they are attached represent C$_{5-6}$-cycloalkyl; or R$^1$ is H and R$^2$ is selected from the group consisting of C$_{1-10}$alkyl, C$_{2-10}$alkenyl, C$_{3-6}$-cycloalkyl, furyl, thienyl, C$_{6-10}$aryl, and C$_{7-14}$aralkyl; R$^3$ is selected from the group consisting of H, —NH$_2$, —NH=CHR$^5$R$^6$, and —NHCHR$^5$R$^6$; wherein R$^5$ and R$^6$ are same or different groups selected from the group consisting of H, C$_{1-10}$alkyl, C$_{2-10}$alkenyl, C$_{3-6}$cycloalkyl, C$_{6-10}$aryl, C$_{7-14}$aralkyl, and heteroaryl; each of the above groups is unsubstituted or substituted with one or more same or different groups selected from the group consisting of C$_{1-5}$alkoxy, hydroxy, amino, C$_{1-5}$alkylamino, di(C$_{1-5}$alkyl)amino, nitro, halogen, C$_{1-5}$-haloalkyl, C$_{1-5}$dihaloalkyl, C$_{1-5}$trihaloalkyl, cyano, C$_{1-5}$alkylthio, mercapto, alkanoyl, carbamoyl, carboxy, and alkanoylamino; the substituent for aryl, aralkyl, and heteroaryl groups additionally includes $C_{1-5}$alkyl; and $R^4$ is selected from the group consisting of H, alkanoyl, aroyl, aralkanoyl, and $P(O)(OM)(OM')$ wherein M and M' are independently selected from the group consisting of H, an alkali metal cation, and phenyl.

2. A compound of claim 1 wherein $R^1$ is H and $R^2$ is methyl, 2-thienyl, or phenyl.

3. A compound of claim 1 wherein $R^3$ is H.

4. A compound of claim 3 wherein $R^1$ is H and $R^2$ is methyl.

5. A compound of claim 4 wherein $R^4$ is H.

6. A compound of claim 4 wherein R is alkanoyl.

7. A compound of claim 6 wherein $R^4$ is octanoyl.

8. A compound of claim 4 wherein $R^4$ is $P(O)(OM(OM')$ wherein M and M' are independently selected from the group consisting of H, an alkali metal, and phenyl.

9. A compound of claim 8 wherein M and M' are the same and are selected from the group consisting of H, alkali metal cation, and phenyl.

10. A compound of claim 1 wherein $R^3$ is $-NH_2$.

11. A compound of claim 10 wherein $R^1$ is H and $R^2$ is methyl.

12. A compound of claim 11 wherein $R^4$ is H.

13. A compound of claim 1 wherein $R^3$ is $-N=CR^5R^6$ and wherein $R^6$ and $R^5$ are the same or different $C_{1-10}$alkyl; or $R^5$ is H and $R^6$ is selected from the group consisting of $C_{1-10}$alkyl, $C_{3-6}$cycloalkyl, $C_{6-10}$aryl, $C_{7-14}$aralkyl, and heteroaryl; the ring portion of the aryl, aralkyl, and heteroaryl groups is unsubstituted or substituted with one or more same or different groups selected from the group consisting of $C_{1-5}$alkyl, $C_{1-5}$alkoxy, hydroxy, amino, $C_{1-5}$alkylamino, di($C_{1-5}$alkyl) amino, nitro, halogen, $C_{1-5}$haloalkyl, $C_{1-5}$dihaloalkyl, $C_{1-5}$trihaloalkyl, cyano, $C_{1-5}$alkylthio, mercapto.

14. A compound of claim 13 wherein $R^6$ and $R^5$ are the same or different $C_{1-3}$alkyl; or $R^5$ is H and $R^6$ is selected from the group consisting of $C_{1-10}$alkyl, phenyl, and phenyl substituted with nitro; and $R^4$ is H or $P(O)(OM)(OM')$ wherein M and M' are independently selected from the group consisting of H, an alkali metal, and phenyl.

15. A compound of claim 14 wherein $R^1$ is H and $R^2$ is methyl.

16. A compound of claim 15 wherein $R^4$ is H.

17. A compound of claim 16 wherein $R^6$ and $R^5$ are the same or different $C_{1-3}$alkyl.

18. A compound of claim 17 wherein $R^5$ and $R^6$ are each methyl.

19. A compound of claim 16 wherein $R^5$ is H and $R^6$ is $C_{1-10}$alkyl.

20. A compound of claim 19 wherein $R^6$ is heptyl.

21. A compound of claim 16 wherein $R^5$ is H and $R^6$ is phenyl.

22. A compound of claim 16 wherein $R^5$ is H and $R^6$ is 4-nitrophenyl.

23. A compound of claim 15 wherein $R^4$ is $P(O)(OM)(OM')$ wherein M and M' are independently selected from the group consisting of H, an alkali metal, and phenyl.

24. A compound of claim 23 wherein $R^4$ is $P(O)(OPh)_2$ where Ph is phenyl, $R^5$ is H, and $R^6$ is phenyl.

25. A compound of claim 1 wherein $R^3$ is $-NHCHR^5R^6$ and wherein $R^5$ and $R^6$ are the same or different $C_{1-10}$alkyl; or $R^5$ is H and $R^6$ is selected from the group consisting of $C_{1-10}$alkyl, $C_{3-6}$cycloalkyl, $C_{6-10}$aryl, $C_{7-14}$aralkyl, and heteroaryl; the ring portion of the aryl, aralkyl, and heteroaryl groups is unsubstituted or substituted with one or more same or different groups selected from the group consisting of $C_{1-5}$alkyl, $C_{1-5}$alkoxy, hydroxy, amino, $C_{1-5}$alkylamino, di($C_{1-5}$alkyl)amino, nitro, halogen, $C_{1-5}$haloalkyl, $C_{1-5}$dihaloalkyl, $C_{1-5}$trihaloalkyl, cyano, $C_{1-5}$alkylthio, mercapto.

26. A compound of claim 25 wherein $R^1$, $R^4$ and $R^5$ are each H, $R^2$ is methyl, and $R^6$ is phenyl.

27. A compound having the formula wherein $R^1$ and $R^2$ are as defined in claim 1 and $R^7$ is $-CN$ or $-C(O)NH_2$.

28. A compound of claim 27 wherein $R^1$ is H and $R^2$ is methyl, phenyl, or 2-thienyl.

29. A compound of claim 28 wherein $R^2$ is methyl.

30. A compound of claim 29 wherein $R^7$ is $-N$.

31. A compound of claim 30 wherein $R^7$ is $-C(O)NH_2$.

32. An intermediate having the formula wherein $R^1$ and $R^2$ are as defined in claim 1; $R^8$ is $-NH_2$ or $-N=CR^5R^6$ wherein $R^5$ and $R^6$ are as defined in claim 1.

33. A compound of claim 32 wherein $R^1$ is H and $R^2$ is methyl.

34. A compound of claim 33 wherein $R^8$ is $-NH_2$.

35. A compound of claim 33 wherein $R^8$ is $-N=CR^5R^6$, and $R^5$ and $R^6$ are same or different groups selected from the group consisting of H, $C_{1-10}$alkyl, $C_{2-10}$alkenyl, $C_{3-6}$cycloalkyl, $C_{6-10}$aryl, $C_{7-14}$aralkyl, and heteroaryl; each of the above groups is unsubstituted or substituted with one or more same or different groups selected from the group consisting of $C_{1-5}$alkoxy, hydroxy, amino, $C_{1-5}$alkylamino, di($C_{1-5}$alkyl)amino, nitro, halogen, $C_{1-5}$haloalkyl, $C_{1-5}$dihaloalkyl, $C_{1-5}$trihaloalkyl, cyano, $C_{1-5}$alkylthio, mercapto, alkanoyl, carbamoyl, carboxy, and alkanoylamino; the substituted for aryl, aralkyl, and heteroaryl groups additionally includes $C_{1-5}$alkyl.

36. A compound of claim 35 wherein $R^5$ and $R^6$ are same or different $C_{1-3}$alkyl.

37. A compound of claim 36 wherein $R^5$ and $R^6$ are each methyl.

38. A compound of claim 35 wherein $R^5$ is H and $R^6$ is selected from $C_{1-10}$alkyl, phenyl, and nitrophenyl.

39. A compound of claim 38 wherein $R^6$ is heptyl.

40. A compound of claim 38 wherein $R^6$ is phenyl.

41. A compound of claim 38 wherein $R^6$ is 4-nitrophenyl.

* * * * *